United States Patent [19]

Moedritzer et al.

[11] Patent Number: 5,536,701
[45] Date of Patent: Jul. 16, 1996

[54] 3-PYRAZOLYLOXYPYRIDAZINES, HERBICIDAL COMPOSITIONS AND USES THEREOF

[75] Inventors: Kurt Moedritzer, Webster Groves; Michael S. South, St. Louis, both of Mo.

[73] Assignee: Monsanto Company, St. Louis, Mo.

[21] Appl. No.: 320,489

[22] Filed: Oct. 11, 1994

[51] Int. Cl.⁶ .................................................. A01N 43/58
[52] U.S. Cl. ................................... 504/238; 544/238
[58] Field of Search ........................... 504/238; 544/238

[56] References Cited

U.S. PATENT DOCUMENTS

| | | | |
|---|---|---|---|
| 3,427,146 | 11/1969 | Tamura et al. | 504/238 |
| 4,251,658 | 2/1981 | Szilagi et al. | 544/238 |
| 4,298,749 | 11/1981 | Plath | 548/377 |
| 4,477,462 | 10/1984 | Aoyagi | 548/376 |
| 4,503,056 | 3/1985 | Haviv | 544/238 |
| 4,772,309 | 9/1988 | Stetter | 504/238 |
| 4,855,442 | 8/1989 | Lee | 548/365 |
| 4,964,895 | 10/1990 | Moedritzer et al. | 548/376 |
| 5,045,106 | 9/1991 | Moedrizer et al. | 548/376 |

FOREIGN PATENT DOCUMENTS

| | | |
|---|---|---|
| 0459333 | 12/1991 | European Pat. Off. . |
| 0459333A1 | 12/1991 | European Pat. Off. . |

OTHER PUBLICATIONS

J. Am. Chem. Soc., G. DeStevens, et al., 81, 6292 (1959).
Derwent Abstract No. 91369 160/50 no date.
J. Heterocyclic Chem., L. Lee et al, 27, 243 (1990).
Chem. Ber., Fehlauer et al, 109, 253 (1976).
F. Elguero, "Comprehensive Heterocyclic Chemicstry", vol. 5; A. Katritzky, ed., Pergamon Press, Oxford (1984) selected pages from pp. 167–303.

*Primary Examiner*—Donald G. Daus
*Attorney, Agent, or Firm*—Grace L. Bonner; Joan V. Thierstein; Dennis R. Hoerner, Jr.

[57] ABSTRACT

Disclosed are certain 3-pyrazolyloxypyridazines, compositions thereof which are herbicidal and methods of using such composition for controlling undesired plants. Also disclosed are mixtures of such pyridazines and acetanilide herbicides, to which mixture a safener may be added, if desired. Intermediate compounds useful in preparing the pyrazolyloxypyridazines are also disclosed.

26 Claims, No Drawings

3-PYRAZOLYLOXYPYRIDAZINES, HERBICIDAL COMPOSITIONS AND USES THEREOF

FIELD OF THE INVENTION

The present invention relates to novel compounds useful for controlling undesired plants and for retarding plant growth. More particularly, the present invention relates to certain pyrazolyloxypyridazines useful for controlling undesired plants and for retarding plant growth.

PRIOR ART

In U.S. Pat. No. 4,964,895, substituted 3-(4-nitrophenoxy)pyrazoles have been disclosed as being useful as herbicides.

In U.S. Pat. No. 3,427,146, certain phenoxy-pyridazines have been disclosed as being useful as herbicides.

5-Amino-4-chloro-2-phenylpyradizin-3-(2H)-one is a known pyridazinone herbicide and has the common name chloridazon.

4-Chloro-5-methylamino-2-(α,α,α-trifluoro-m-tolyl)pyridazin- 3-(2H)-one is another known pyridazinone herbicide and has the common name norflurazon.

6-Chloro-3-phenylpyridazin-4-yl-S-octyl thiocarbonate is a known pyridazine herbicide and has the common name pyridate.

There is a continuing need in the art for herbicides which provide a broad spectrum of control of weeds and which may be better tolerated by crops. The present invention provides such kind of improved and useful herbicides.

SUMMARY OF THE INVENTION

The novel compounds of the present invention may be depicted by one of the following structural formulas:

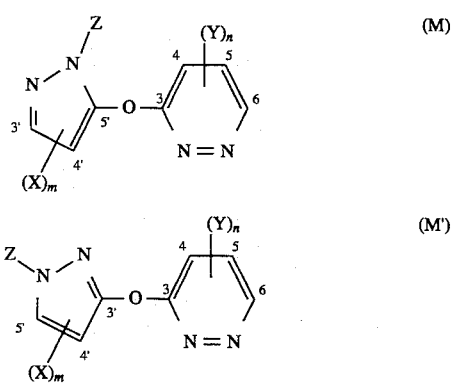

wherein:

Z is hydrogen, $C_1$–$C_{10}$ alkyl, $C_1$–$C_3$ haloalkyl, phenyl, phenyl $C_1$–$C_7$ alkyl or tetrahydropyranyl;

X is hydrogen, $C_1$–$C_7$-haloalkyl, halo, $C_1$–$C_{10}$ alkyl, $C_1$–$C_7$ alkenyl, $C_1$–$C_7$ alkynyl, $C_1$–$C_7$ alkoxy, $C_1$–$C_7$alkylthio, $C_1$–$C_7$ alkylsulfinyl, $C_1$–$C_7$ alkyloxycarbonyl, $C_1$–$C_7$ alkylsulfonyl, phenyl, phenyl $C_1$–$C_7$ alkyl, hydridocarbonyl, cyano, hydroxycarbonyl, mono or di-Cl-$C_7$ alkoxy $C_1$–$C_7$ alkyl, amino, aminocarbonyl, phenylaminocarbonyl, $C_1$–$C_7$ alkyldi $C_1$–$C_7$ alkylsilyl, mono or di $C_1$–$C_7$ alkyl-aminocarbonyl, nitro, $C_1$–$C_7$ haloalkyl-dioxolan-2yl, $C_1$–$C_7$haloalkoxycarbonyl, $C_1$–$C_7$ haloalkylcarbonyl, $C_1$–$C_7$ haloalkenyl, hydroxy $C_1$–$C_7$ alkyl, phenyl $C_1$–$C_7$ alkoxy, $C_1$–$C_7$haloalkoxy, $C_1$–$C_7$ alkylcarbonyl, hydroxyhalo $C_1$–$C_{10}$ alkyl, $C_1$–$C_7$ alkoxy $C_1$–$C_7$ alkyl $C_1$–$C_7$ alkylamino $C_1$–$C_7$alkenyl or m is zero or an integer of 1 or 2; when m is 2, each X may be the same or different;

either N in the pyridazine ring is optionally substituted with N-oxide;

Y is hydrogen, $C_1$–$C_7$-haloalkyl, halo, $C_1$–$C_7$ alkoxy, cyano, $C_1$–$C_7$ alkylthio, mono or di-$C_1$–$C_7$ alkylamino, hydroxy, $C_1$–$C_7$ haloalkoxy, $C_1$–$C_{10}$ alkyl, $C_1$–$C_7$ alkenyl, $C_1$–$C_7$ alkynyl or the same substituent as in the 3-position of the pyridazine ring;

n is zero or an integer of 1, 2 or 3; when n is 2 or 3, each Y may be the same or different; and agriculturally acceptable salts of such compounds.

The term "Formula M" is intended to include both formulas M and M' alone which depict the two isomeric forms of the pyrazole moiety of the novel compounds herein.

The present invention provides novel compounds of the general Formula M depicted above which exhibit desirable herbicidal properties and further provides herbicidal compositions for the selective controlling of weeds in crop plants. The compositions comprise one or more compounds of Formula M herein by themselves or admixed with one or more carriers, such as solid and/or liquid inert extenders or diluents and/or wetting agents and optionally other active herbicides, insecticides, fungicides, safeners, growth regulators, plant nutrients and like additaments. The invention also provides an effective method of controlling undesirable plants, such as grasses, perennial and annual broadleafed weeds and so on which comprises applying to the locus of the plants to be controlled an effective amount of at least one pyrazolyloxypyridazine to exert a herbicidal action.

These novel pyrazolyloxypyridazine compounds which may be employed as an active ingredient in this invention can be prepared by a variety of new and useful processes, such as one of the general procedures as will be described below. Many of the depicted intermediate compounds are novel and useful for preparing the herbicidal pyrazolyloxypyridazines herein.

DETAILED DESCRIPTION OF THE INVENTION

It has been shown that the pyrazole oxygen-linked pyridazine compounds within the above depicted general Formula M are not only herbicidal against undesired plants but also have good herbicidal tolerance by certain crop plants, especially corn. Novel compounds herein in many instances provide substantially equal or better herbicidal performance than the present widely commercially employed acetanilides but with better environmental acceptability. The preferred compounds herein provide a broader spectrum of weed control and show good perennial broadleaf activity. The field soil half-life of the preferred compounds provides longer residual control than alachlor but is normally short enough that any carryover problems are agronomically acceptable.

In this specification and claims, numerical values are not critical unless otherwise stated. That is, the numerical values may be read as if prefaced with the word "about" or "substantially".

The following defines the various terms used in the application.

The term "$C_1$–$C_{10}$ alkyl" or in the shortened form "$C_1$–$C_{10}$ alkyl" as used herein include the straight and branched aliphatic groups of one to ten carbon atoms, such as methyl, ethyl, propyl, isopropyl (1-methylethyl), butyl, isobutyl, (2-methylpropyl), sec-butyl, (1-methylpropyl), tert-butyl, (1,1-dimethylethyl), pentyl, isopentyl, (3-methylbutyl), sec-pentyl (1-methylbutyl), 1,1-dimethylpropyl, 1-2-dimethylpropyl, neopentyl, (2,2-dimethylpropyl), hexyl, isohexyl (4-methylpentyl), sec-hexyl, (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The terms, such as "$C_1-C_3$" and "$C_1-C_5$" are included in the term $C_1-C_{10}$ but with a corresponding lesser number of carbon atoms as indicated.

The term "$C_1-C_3$ haloalkyl" as used herein includes such radicals as trifluoromethyl, trichloromethyl, difluoromethyl, chlorodifluoromethyl, fluoromethyl, bromomethyl, pentafluoroethyl, heptafluoro-n-propyl, pentachloroethyl, iodomethyl, etc., where the number of carbon atoms in the alkyl is 1–3, inclusive.

The term "halogen" either alone or in compound words such as "haloalky" denotes fluorine, chlorine, bromine or iodine.

The term "alkoxy" denotes methoxy, ethoxy, n-propyloxy, isopropyloxy and the different butoxy, pentoxy, hexoxy isomers, etc.

The term "alkenyl" denotes straight or branched alkenes, e.g., vinyl, 1-propenyl, 2-propenyl, and the different butenyl, pentenyl, hexenyl isomers, etc.

The term "alkynyl" denotes straight chain or branched alkynes, e.g., ethynyl, 1-propynyl, 2-propynyl, etc., including the different butynyl, pentynyl and hexynyl isomers.

The term "alkylthio" denotes methylthio, ethylthio and the various propylthio, butylthio, pentylthio and hexylthio isomers.

Alkylsulfinyl, alkylsulfonyl, alkylamine, etc., are defined analogously to the above terms.

A process for preparing the compounds of the present invention can be described in the following schematic diagrams which follow below.

The compounds according to this invention are suitably prepared by a variety of processes as will also be described below with greater particularity.

In broad aspect, the preferred overall process for preparing the compounds of Formula M is best viewed in the separate process steps required to prepare the necessary intermediates, immediate precursors and end products of the above formula. The products of "Process I and Process II" provide the intermediates necessary for "Process III". The compounds according to Formula M are prepared by either a single process "II–III" or any suitable combination of "Processes I–III". It is expressly understood that various modifications obvious to those skilled in the art are contemplated. Specific embodiments of the preparation of the compounds herein are described in Examples 1–20 below.

In the sequence of process steps described below, the various symbols defining radical substituents, e.g., X, Y, Z, m, n, etc., have the same meanings as defined for the compounds of Formula M, unless otherwise qualified or limited.

Process I—Intermediate Preparation

This process describes the preparation of important intermediate compounds of Formula F structurally depicted below which are useful in the overall following process scheme for producing compounds of Formula F which are intermediate compounds of Formula M.

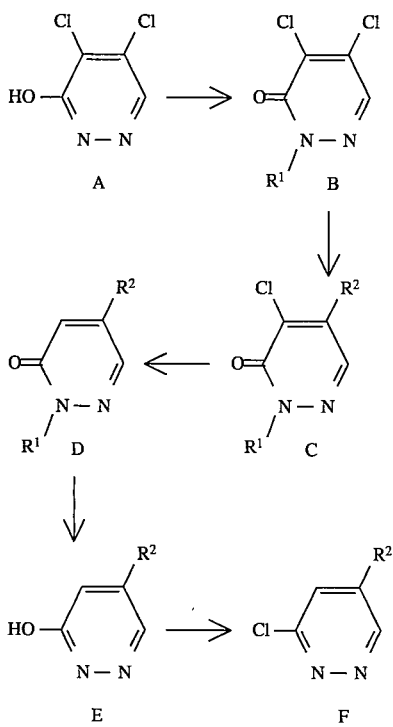

Scheme 1

In the first step in the process for the preparation of precursor compounds of Formula F one can use 3,4-dichloro-5-hydroxypyridazine as the starting material (Formula A Compound), which is commercially available and known in the art. Treatment of the compound of Formula A with an appropriate protecting group chosen, among other compounds, from chloromethylmethyl ether, chloromethylthiomethyl ether, or 2-methoxyethoxymethyl chloride and an organic or inorganic acid, such as p-toluenesulfonic acid or sulfuric acid, or dihydropyran and an organic base chosen from compounds, such as triethylamine or N,N-diisopyropylethylamine gives a pyridazone compound of Formula B. In compounds of Formula B, $R^1$ is derived from one of the protecting groups mentioned above. The reaction can be carried out in any suitable anhydrous solvent or mixture of suitable solvents with the preferred solvents being chosen from ether, tetrahydrofuran (THF), benzene, toluene, or methylene chloride. The reaction temperatures may range from –78° C. to 150° C., preferably 0° C. to 100° C. The reaction period may be chosen from a few minutes to several weeks depending on the amounts of reagents, reaction temperature, etc. After the reaction is complete, the mixture containing the compounds of Formula B is diluted with an appropriate organic solvent and extracted with an aqueous base, such as sodium bicarbonate. The compounds of Formula B are isolated by drying the organic solvent, filtration, and then removal of the solvent in vacuo. The compounds of Formula B can be utilized as is; or, if necessary, they may be purified by standard methods, such as crystallization or column chromatography.

The second step in Process I involves the conversion of compounds of Formula B to compounds of Formula C by treatment of Compound B with an alkyl, aryl, or heterocyclic alcohol, thiol, or amine and an appropriate base, such as sodium hydroxide, potassium hydroxide, sodium hydride, potassium hydride, sodium bicarbonate, potassium carbonate, triethylamine, N,N-diisopyropylethylamine, or 1,8-diazabicyclo-[5.4.0]-undec- 7-ene (DBU) to give compounds of Formula C. In compounds of Formula C, $R^2$ is derived from the alkyl, aryl, or heterocyclic alcohol, thiol, or amine mentioned above and in many cases will be equivalent to substituent Y of Formula M. The reaction can be carried out neat with the above mentioned alcohol, thiol, or amine as solvent or in any suitable anhydrous solvent or mixture of solvents with the preferred solvents being chosen from diethyl ether, THF, benzene, N,N-dimethylformamide (DMF), or dimethylsulfoxide. The reaction temperatures may range from −78° C. to 150° C., preferably −20° C. to 100° C. The reaction period may be chosen from a few minutes to several weeks depending on the amounts of reagents, reaction temperature, etc. The resulting reaction mixture containing the compounds of Formula C are then diluted with a suitable inert organic solvent and extracted several times with water. The compounds of Formula C are isolated by removal of the organic solvent in vacuo and may be used as is or, if necessary, may be purified by standard methods, such as crystallization or column chromatography.

The third step in Process I involves the conversion of compounds of Formula C to compounds of Formula D by treatment of compounds of Formula C with hydrogen, in the presence of a catalytic amount of an appropriate transition metal catalyst such as Pd-C, Pt-C, or $PtO_2$, and an appropriate base, such as triethylamine, N,N-diisopyropylethylamine, or DBU, to give compounds of Formula D. The reaction can be carried out in a suitable anhydrous solvent or mixture of solvents with the preferred solvents being chosen from methanol, ethanol, benzene, or ethyl acetate, preferably methanol or ethanol. The reaction temperatures may range from −78° C. to 150° C., preferably 0° C. to 40° C. The reaction period may be chosen from a few minutes to several weeks depending on the amounts of reagents, reaction temperature, etc. The compounds of Formula D are isolated by filtration and removal of the solvent in vacuo. The compounds of Formula D are used as is or may be purified by standard methods, such as crystallization or column chromatography.

The fourth step in Process I involves the conversion of compounds of Formula D to compounds of Formula E by treatment of compounds of Formula D with a strong aqueous acid, such as hydrochloric acid, phosphoric acid, sulfuric acid, or nitric acid to give compounds of Formula E. The reaction is carried out in the aqueous acid as solvent in the presence of a co-solvent such as methanol, ethanol, or THF with the reaction temperatures ranging from 0° C. to 100° C., preferably 25° C. to 100° C. The reaction period may be chosen from a few minutes to several weeks depending on the amounts of reagents, reaction temperature, etc. The compounds of Formula E are isolated by making the reaction mixture basic with sodium hydroxide, or other suitable base, extracting with a chlorinated solvent, such as methylene chloride, chloroform, or carbon tetrachloride to remove contaminants and then acidifying with concentrated acid to precipitate the product. The products of Formula E are then collected by filtration and dried and may be used, as is, or if necessary purified by standard methods, such as crystallization or column chromatography.

The fifth step in Process I involves the conversion of compounds of Formula E to compounds of Formula F by treatment of compounds of Formula E with a chlorinating agent, such as thionyl chloride, oxalyl chloride, sulfuryl chloride, or phosphorus oxychloride to give compounds of Formula F. The reaction may be carried out neat in the chlorinating agent as solvent or with the chlorinating agent and a co-solvent, such as methylene chloride, chloroform, or carbon tetrachloride. The reaction temperature may range from 0° C. to 100° C., preferably 25° C. to 100° C. The reaction period may be a few minutes to several weeks depending on the amounts of reagents, reaction temperature, etc. The compounds of Formula F are isolated by removal of the solvents in vacuo to give the compounds of Formula F which can be used, as is, or purified by standard methods, such as crystallization or column chromatography.

Process II—Intermediate Preparation

This process describes the preparation of important intermediate compounds of Formula H, Formula I and Formula J which are useful in the following overall process scheme for producing intermediate compounds of Formula I.

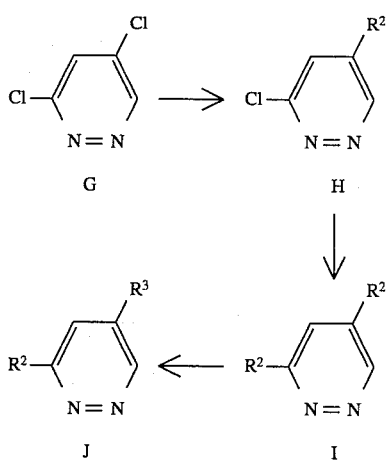

Scheme 2

The first and second steps of Process II involve the conversion of 3,5-dichloropyridazine (Formula G), which process is generally known in the art (W. Deinhammer et al, German Patent No. 2,706,701, 1978), to compounds of Formula H by treatment with one equivalents or two equivalents of the following nucleophiles to compounds of Formula I by treatment with a corresponding number of equivalents of an alkyl, aryl, or heterocyclic alcohol, thiol, or amine and an appropriate base, such as sodium hydroxide, potassium hydroxide, sodium hydride, potassium hydride, sodium bicarbonate, potassium t-butoxide, sodium methoxide, potassium carbonate, triethylamine, N,N-diisopyropylethylamine or DBU. In compounds of Formula H or I, $R^2$ can be derived from a suitable alkyl, aryl or heterocyclic alcohol, thiol, or amine mentioned above and in many cases would be equivalent to substituent Y of Formula M. The reaction can be carried out neat with the above mentioned alcohol, thiol, or amine as solvent or in any anhydrous solvent or mixture of solvents with the preferred solvents being chosen from ether, THF, benzene, DMF, or dimethylsulfoxide. The reaction temperatures may range from −78° C. to 150° C., preferably −20° C. to 100° C. The reaction period may be chosen from a few minutes to several weeks depending on the amounts of reagents, reaction temperature, etc. The mixture containing the compounds of Formula H or I is then diluted with an organic solvent and extracted several times with water. The compounds of Formula H or I are isolated by removal of the organic solvent in vacuo and may be used, as is, or if necessary may be purified by standard methods, such as crystallization or column chromatography.

The third step of Process II involves the conversion of compounds of Formula I to compounds of Formula J by treatment of compounds of Formula I, where $R^2$ is defined as an aryl, or heterocyclic alcohol, thiol, or amine, with a suitable base, such as sodium hydroxide potassium t-butoxide, sodium methoxide or potassium hydroxide to give compounds of Formula J, where $R^3$ is hydroxyl or other radical of suitable functionality. The reaction can be carried out in an aqueous solution of a base with the addition of a co-solvent, such as dimethylsulfoxide or DMF. The reaction temperatures may range from −78° C. to 150° C., preferably 0° C. to 100° C. The reaction period may be chosen from a few minutes to several weeks depending on the amounts of reagents, reaction temperature, etc. The compounds of Formula J can be isolated by extraction with an organic solvent which is removed in vacuo to give the products which may be used, as is, or purified by standard methods, such as crystallization or column chromatography. Before extraction, excess base can be neutralized by the addition of a suitable acidifying agent.

It is understood that compounds of Formula J, where $R^3$ is hydroxyl, may be converted to additional products by treatment with a base chosen from sodium hydride, potassium hydride, sodium bicarbonate, potassium t-butoxide, sodium methoxide, potassium carbonate, triethylamine, N,N-diisopyropylethylamine, or DBU and an alkyl, aryl, or heterocyclic halide or sulfonate to give compounds of Formula J where $R^3$ is in many cases equivalent to substituent Y of Formula M and $R^2$ is equivalent in many cases to the pyrazole moiety with substituent X of Formula M. The reaction may be carried out in any suitable anhydrous solvent or mixture of solvents, preferably ether, tetrahydrofuran, N,N-dimethylformamide, or dimethylsulfoxide. The reaction temperatures may range from −78° C. to 150° C., preferably 0° C. to 100° C. The reaction period may be chosen from a few minutes to several weeks depending on the amounts of reagents, reaction temperature, etc. The compounds of Formula J are isolated by extraction with an organic solvent which is removed in vacuo to give the products which may be used, as is, or purified by standard methods, such as crystallization or column chromatography. Before extraction, excess base can be neutralized by the addition of a suitable acidifying agent.

Process III—Intermediate Preparation

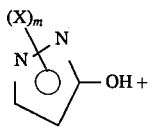

K

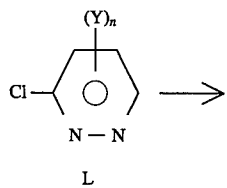

L

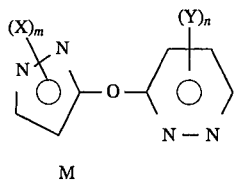

M

Scheme 3

This process describes the preparation of compounds of Formula M. Pyrazoles of Formula K, which are known in the art and are usually prepared from various substituted 1,3-ketoesters and substituted hydrazines or various 3-substituted propiolates and substituted hydrazines (for representative examples see: B.C. Hamper et al J. Fluorine Chem., 48, 123 (1990); Moedritzer et al U.S. Pat. Nos. 4,964,895 and 5,045,106; Lee et al U.S. Pat. No. 4,855,442, G. DeStevens, et al., J. Am. Chem. Soc., 81, 6292 (1959); L. Lee et al J. Heterocyclic Chem., 27, 243 (1990); E. Aoyagi U.S. Pat. No. 4,477,462; A. Fehlauer et al., Chem. Ber., 109, 253 (1976); F. Elguero, "Comprehensive Heterocyclic Chemistry", Vol. 5; A Katritzky, ed , Pergamon Press, Oxford (1984) (pp 167–303), and pyridazines of Formula L, which are either known in the art, commercially available, or prepared as described herein above, are combined together with an appropriate base chosen preferably from sodium hydride, potassium hydride, potassium t-butoxide, sodium methoxide, sodium bicarbonate, potassium carbonate, triethylamine, N,N-diisopyropylethylamine, 2,6-1utidine, or DBU, and optionally an appropriate catalyst chosen from $TiCl_4$, $SnCl_2$, $FeCl_3$, CuCl, CuBr, $AgBF_4$, or CuF to give compounds of Formula M. In these cases X and Y are defined as given above for Formula M". The reaction may be carried out in any anhydrous solvent or mixture of solvents, preferably ether, tetrahydrofuran, N,N-dimethylformamide, dimethylsulfoxide, diglyme, glyme, sulfolane, benzene, toluene, or xylene. The reaction temperatures may range from −78° C. to 200° C., preferably 0° C. to 180° C. The reaction period may be chosen from a few minutes to several weeks depending on the amounts of reagents, reaction temperature, etc. The products of Formula M" are isolated by diluting the reaction mixture with an organic solvent and extracting with Water. The organic solvent is then removed in vacuo and the products of Formula M are either used, as is, or purified by standard methods, such as crystallization or chromatography, etc.

The acid addition salts useful in the present composition can be prepared by admixing a suitable pyrazolyloxypyridazine with a suitable acid to form the corresponding acid addition salt. Examples of those acids which may be employed include inorganic acids, such as hydrochloric acid, sulfuric acid, nitric acid, phosphoric acid and an organic acid such as trichloroacetic acid. It is to be noted that certain pyrazolyloxypyridazines cannot be converted conveniently to a suitable corresponding acid addition salt.

Preparations of some intermediates of the compounds of this invention and the compounds of this invention are illustrated by the following examples. In the examples which follow all percentages are given on a weight basis unless otherwise indicated.

EXAMPLE 1

This example describes the preparation of 3-chloro-5-methoxypyridazine which is used as an intermediate in Process II and/or Process III.

A. 4,5-Dichloro-3-hydroxypyridazine (3000 g, 18.18 moles), dihydropyran (1943 g, 23.08 moles), p-toluenesulfonic acid monohydrate (283 g, 1.49 moles), and 16 L of tetrahydrofuran were added to a 50 L round bottomed flask equipped with a heating mantle, reflux condenser, and a mechanical stirrer. The mixture was stirred at reflux for 29 h. Additional dihydropyran was added at 6 h (1328 g, 15.79 moles) and at 21 h (780 g, 9.25 moles). The reaction mixture was allowed to cool to room temperature overnight. The mixture was concentrated in vacuo to an oily residue. The residue was taken up in 16 L of ethyl acetate and washed with 2N NaOH (2×6 L). The organic solution was dried ($MgSO_4$) and concentrated in vacuo to give 4,5-dichloro-2-(tetrahydro- 2H-pyran-2-yl)-3(2H)-pyridazinone which was a black oily solid which was used without further purification in the next step. A portion of the product was purified by filtration through silica gel with ethyl acetate followed by evaporation and recrystallization from ethyl acetate/cyclohexane to give a white solid, mp=74°–76° C. Anal. Calc. for $C_9H_{10}N_2O_2Cl_2+0.1\ C_6H_{12}$: C, 44.78; H, 4.38; N, 10.89 Found: C, 44.63; H, 4.22; N, 10.94

B. 4,5-Dichloro-2-(tetrahydro-2H-pyran-2-yl)-3(2H)-pyridazinone from the previous step and 17 L of methanol were added to a 50 L round bottomed flask equipped with a glycol cooling jacket and a mechanical stirrer. The resulting solution was cooled to 0° C. and 87% KOH (1172 g 18.17 moles) was added in portions over approximately 1 h. The mixture exothermed to 40° C. Following the addition the mixture was allowed to stir an additional 3 h at ambient temperature. The reaction mixture was partitioned with 12 L of ethyl acetate and 12 L of $H_2O$. The aqueous layer was extracted with ethyl acetate (2×4 L). The combined organic layers were washed with brine (2×10 L) and dried ($MgSO_4$). The organic solution was clarified by filtration and concentrated to give a dark semi-solid. The crude material was equally divided and added to two 22 L flasks. The material was suspended in 12 L hexane/diethyl ether (2:1 ratio). The washed material was vacuum filtered on a Büchner funnel and air dried overnight to give 3,406 g (77% over 2 steps) of 4-chloro- 5-methoxy-2-(tetrahydro-2H-pyran-2-yl)-3(2H)-pyridazinone as a dark tan solid suitable for further transformations. The product was purified by recrystallization from ethyl acetate/cyclohexane to give a white solid, mp=118°–120° C.

Anal. Calc. for $C_{10}H_{13}N_2O_3Cl$: C, 49.09; H, 5.36; N, 11.45 Found: C, 49.04; H, 5.38; N, 11.43

C. 4-Chloro-5-methoxy-2-(tetrahydro-2H-pyran-2-yl)-3(2H)-pyridazinone (2486 g, 10.16 moles), ethanol (8 L), triethylamine (2L, 14.23 moles), and 5% Pd-C (100 g of 50% water-wet Pd-C) were added to a 22 L autoclave. The mixture was hydrogenated at 50–60 psi (345–414 kilopascals) of $H_2$ and heated to a maximum temperature of 43° C. After 24 h, the reaction was complete. The reaction mixture was diluted with a small amount of water and vacuum filtered through celite. The filtrate was concentrated and partitioned with 10 L of ethyl acetate and 8 L of $H_2O$. The aqueous phase was extracted with ethyl acetate (2×2 L). The combined organics were washed with 5 L brine, dried ($MgSO_4$), and vacuum filtered. The solution was concentrated in vacuo to give 2133 g (100% yield) of 5-methoxy-2-(tetrahydro-2H-pyran- 2-yl)-3(2H)-pyridazinone as a dark oil which later crystallized to give a tan product suitable for further transformations. The product was purified by recrystallization from ethyl acetate/cyclohexane to give a white solid, mp=76°–78° C.

Anal. Calc. for $C_{10}H_{14}N_2O_3$: C, 57.13; H, 6.71; N, 13.32 Found: C, 56.86; H, 6.61; N, 13.21

D. 5-Methoxy-2-(tetrahydro-2H-pyran-2-yl)-3(2H)-pyridazinone (2035 g, 9.69 moles) and 2 L of methanol were added to a 22 L round bottomed flask equipped with a heating mantle, reflux condenser and mechanical stirrer. The mixture was warmed to 35° C. and 8 L of 6 N HCl was added and then the mixture was heated to reflux for 2 h. The reaction mixture was then cooled slightly and transferred to a glycol cooled 22 L flask where the mixture was cooled further to 30° C. The mixture was made basic (pH 13–14) by cautious addition of 50% NaOH in portions. The basic mixture was extracted with $CH_2Cl_2$ (4×3 L). The aqueous phase was then acidified with concentrated HCl (pH 1–2) to precipitate the product. The product was collected by vacuum filtration on a Büchner funnel. The product was dried to constant weight on a fluid bed dryer at 70° C. This afforded 798 g (65% yield) of 3-hydroxy-5-methoxypyridazine as a white solid which was recrystallized from methanol, mp=253°–255° C.

Anal. Calc. for $C_5H_6N_2O_2$:

C, 47.62; H, 4.80; N, 22.21 Found: C, 47.60; H, 4.83; N, 22.18

E. 3-Hydroxy-5-methoxypyridazine (629.6 g, 4.99 moles) and phosphorus oxychloride (2.5 L, 27 moles) were added to a 5 L round bottomed flask equipped with a heating mantle and a mechanical stirrer. The resulting stirred slurry was rapidly heated (<30 min) to 75° C. At this temperature the heating mantle was removed. The reaction mixture continued to exotherm to a final temperature of 82.3° C. After the solids had dissolved in the darkening reaction mixture, stirring was continued an additional 2 minutes. The homogeneous reaction mixture was then rapidly cooled to room temperature with an ice/water bath. The reaction mixture was concentrated via rotary evaporator using pump vacuum and a water bath temperature of 45° C. The residue was taken up in 2 L of $CH_2Cl_2$ and slowly poured into a stirring mixture of 2 L $CH_2Cl_2$ and 6 L of $H_2O$ chilled to 10° C. The layers were separated and enough 50% NaOH was added to the aqueous phase to give a pH of 2–4. The aqueous phase was extracted with additional $CH_2Cl_2$ (2×2 L). The combined organic layers were washed with 4 L of $H_2O$ and dried ($MgSO_4$). The solution was vacuum filtered through 1 kg of silica gel. The silica gel was washed with 4 L of ethyl acetate/hexane (1:1). The filtrate was concentrated in vacuo to afford 564 g (78% yield) of 3-chloro-5-methoxypyridazine as a pale yellow solid. The product was stored in a freezer to prevent gradual decomposition. The product was recrystallized from ethyl acetate/cyclohexane to give a white solid, mp=98°–100° C.

Anal. Calc. for $C_5H_5N_2OCl$:

C, 41.54; H, 3.49; N, 19.38 Found: C, 41.62; H, 3.51; N, 19.34

EXAMPLE 2

This example describes the preparation of 3,5-bis[[1-methyl-3-(trifluoromethyl)-1H-pyrazol-5-yl]oxy]-pyridazine (Compound No. 11).

1-Methyl-3-(trifluoromethyl)-1H-pyrazol-5-ol (7.07 g, 0.043 mole) which is known in the art, 3,5-dichloropyridazine (3.00 g, 0.020 mole), CuBr (2.91 g, 0.020 mole), potassium carbonate (8.40 g, 0.061 mole), and dry dimethylsulfoxide (100 mL were stirred under $N_2$ at 100° C. for 2 h. The mixture was then poured into saturated ammonium chloride and extracted 3×100 mL with ethyl acetate. The combined organic layers were then extracted 2 times with saturated sodium bicarbonate solution, dried ($MgSO_4$), filtered through silica gel with ethyl acetate and evaporated in vacuo to give 3,5-bis-[[1-methyl-3-(trifluoromethyl)--1H-pyrazol-5-yl]oxy]-pyridazine (4.72 g, 57% yield). This solid was recrystallized from ethyl acetate/cyclohexane to give a white solid.

EXAMPLE 3

This example describes the preparation of N-methyl-6-[[1-methyl-3-(trifluoromethyl)-1H-pyrazol-5-yl]oxy]-4-pyridazinamine (Compound No. 10).

3,5-Bis[[1-methyl-3-(trifluoromethyl)-1H-pyrazol-5-yl]oxy]pyridazine (Compound No. 11, 1.50 g, 0.004 moles) and methylamine (3.1 mL of a 40% aqueous solution, 0.04 mole) were refluxed under $N_2$ in tetrahydrofuran (100 mL) for 24 h. The mixture was then partitioned between ethyl acetate and water. The organic layer was dried ($MgSO_4$), filtered and evaporated to give a crude solid which was purified by silica gel chromatography. N-Methyl-6-[[1-methyl-3-(trifluoromethyl)-1H-pyrazol-5-yl]oxy]-4-pyridazinamine (0.6 g, 55% yield) was obtained as a light brown solid which was recrystallized from ethyl acetate/cyclohexane.

EXAMPLE 4

This example describes the preparation of 6-[[1-methyl-3-(trifluoromethyl)-1H-pyrazol-5-yl]oxy]-4-pyridazinol (Compound No. 12).

3,5-Bis[[1-methyl-3-(trifluoromethyl)-1H-pyrazol-5-yl]oxy]pyridazine (Compound No. 11, 3.0 g, 0.0073 mole) and 2.5N NaOH (14.7 mL, 0.0367 mole) were stirred in dimethylsulfoxide (45 mL) at room temperature under $N_2$ for 15 minutes. The mixture was then heated to 80° C. for 5 minutes. The mixture was cooled to room temperature and allowed to stir for 1 h. The mixture was then poured into water and made acidic with 12N HCl. The mixture was extracted 3×200 mL with ethyl acetate and the organic layer was dried ($MgSO_4$), filtered and evaporated in vacuo. The residue was triturated with a minimum amount of ethyl acetate and filtered to collect the product. The mother liquor was condensed and this process was repeated two more times. 6-[[1-Methyl-3-(trifluoromethyl)-1H-pyrazol-5-yl]oxy]-4-pyridazinol (1.35 g, 71% yield) was obtained as a white solid.

EXAMPLE 5

This example describes the preparation of 5-(difluoromethoxy)- 3-[[1-methyl-3-(trifluoromethyl)-1H-pyrazol-5-yl]oxy]pyridazine (Compound No. 13) and 5-ethoxy-3-[[1-methyl-3-(trifluoromethyl)-1H-pyrazol-5-yl]oxy]pyridazine (Compound No. 14).

6-[[1-Methyl-3-(trifluoromethyl)-1H-pyrazol-5-yl]oxy]-4-pyridazinol (Compound No. 12, 1.0 g, 0.0038 mole) and NaH (1.15 g of 80% NaH in oil, 0.0384 mole) were heated to 80° C. in DMF (20 mL) while $CF_2ClH$ was continuously bubbled through the solution for 6.5 h. The mixture was cooled to 0° C. and quenched by dropwise addition of water under an $N_2$ sweep. After $H_2$ ceased to evolve the mixture was poured into water/ethyl acetate and made acidic with excess ammonium chloride and then extracted 3×100 mL with ethyl acetate. The organic layers were extracted with brine, dried ($MgSO_4$), filtered through silica gel with ethyl acetate, and evaporated in vacuo. Two compounds were present as evidenced by TLC. The mixture was separated by reverse phase chroma-tography to give 5-(difluoromethoxy)-3-[[1-methyl-3-(trifluoromethyl)-1H-pyrazol-5-yl]oxy]pyridazine (0.144 g, 12% yield) as a yellow solid (mp=86 –88° C.) and 5-ethoxy-3-[[1-methyl-3-(trifluoromethyl)-1H-pyrazol-5-yl]oxy]pyridazine (0.058 g, 5% yield as a yellow solid.

EXAMPLE 6

This example describes the preparation of 3-[[4-chloro-1-methyl-5-(methylthio)-1H-pyrazol-3-yl]oxy]-5-methoxypyridazine (Compound No. 28).

4-Chloro-1-methyl-5-(methylthio)-1H-pyrazol-3-ol which is a known compound (2.7 g, 0.015 mole), 3-chloro-5-methoxypyridazine (1.45 g, 0.01 mole), and 2,6-lutidine (1.4 mL, 0.012 moles) were heated to reflux in toluene (40 mL) under $N_2$ for 18 h. The mixture was then poured into aqueous ammonium chloride and extracted 3×100 mL with ethyl acetate. The organic layers were washed with water and brine, dried ($MgSO_4$), filtered and evaporated in vacuo. The crude solid was purified by flash chromatography to give 3-[[4-chloro-1-methyl-5-(methylthio)-1H-pyrazol-3-yl]oxy]-5-methoxypyridazine (1.1 g, 26% yield) as a white solid.

EXAMPLE 7

This example describes the preparation of 5-methoxy-3-[[1-methyl-3-(trifluoromethyl)-1H-pyrazol-5yl-]oxy]pyridazine (Compound No. 5).

1-Methyl-3-(trifluoromethyl)-1H-pyrazol-5-ol (4.0 g, 0.024 mole), 3-chloro-5-methoxypyridazine (3.5 g, 0.024 mole), and 2,6-1-lutidine (3.0 g, 0.028 mole) were heated to reflux in toluene (75 mL) under $N_2$ and held there for 22.5 h. The mixture was poured into diluted HCl (1%) aqueous solution and extracted 2×100 mL with ethyl acetate. The organic layer was extracted with brine followed by dilute NaOH (1%, 2×100 mL). The organic layer was dried ($MgSO_4$), filtered through silica gel with ethyl acetate and evaporated in vacuo to give 5-methoxy-3-[[1-methyl-3-(trifluoromethyl)-1H-pyrazol-5-yl]oxy]-pyridazine (6.25 g, 95% yield) as a light brown solid. This solid was recrystallized from ethyl acetate/cyclohexane.

EXAMPLE 8

This example describes the preparation of 5-methoxy-3-[[1-methyl-3-(pentafluoroethyl)-1H-pyrazol-5-yl]oxy]pyridazine (Compound No. 18).

A. The preparation of this pyrazole is representative of many of the pyrazoles used herein. Ethyl 4,4,5,5,5-pentafluoropropionylacetate (100 g, 0.427 mole) which is known in the art and methylhydrazine (20.66 g, 0.448 mole) were added to ethanol (400 mL). A mild exotherm to 30° C. was controlled with a cold water bath. The mixture was then stirred under $N_2$ at room temperature for 31 h and then refluxed for 12 h. The solvent was removed in vacuo and the residue was recrystallized from ethyl acetate/cyclohexane to give 1-methyl-3-(pentafluoroethyl)-1H-pyrazol-5-ol (48.52 g, 53% yield) as a white solid (mp=183°–188° C.).

Anal. Calc. for $C_6H_5N_2OF_5$:

C, 33.35; H, 2.33; N, 12.96 Found: C, 33.25; H, 2.34; N, 12.93

B. 1-Methyl-3-(pentafluoroethyl)-1H-pyrazol-5-ol (0.44 g, 0.002 mole), 3-chloro-5-methoxypyridazine (0.29 g, 0.002 mole), and 2,6-lutidine (0.27 g, 0.0024 mole) were refluxed under $N_2$ in toluene (8 mL) for 15 h. This mixture was poured into ethyl acetate and washed with 7% HCl, water and then with saturated sodium bicarbonate. The organic layer was dried (MgSO$_4$), filtered through silica gel with ethyl acetate, and evaporated in vacuo to give 5-methoxy-3-[[1-methyl-3-(pentafluoroethyl)-1H-pyrazol-5-yl]oxy]pyridazine as a light yellow solid. The compound was recrystallized to give (0.45 g, 69% yield) Compound 18, a white solid.

EXAMPLE 9

This example describes the preparation of 3-[[3-(1,1-dimethylethyl)-1-methyl-1H-pyrazol-5-yl]oxy-5-methoxypyridazine (Compound No. 17).

3-(1,1-Dimethylethyl)-1-methyl-1H-pyrazol-5-ol (1.12 g, 0.0073 moles) which is a known compound, 3-chloro-5-methoxypyridazine (1.02 g, 0.0071 mole), potassium carbonate (1.87 g, 0.0136 mole), and CuBr (1.05 g, 0.0073 mole) were added to dry dimethyl-sulfoxide (12 mL). The mixture was stirred under N$_2$ at 95° C. for 7 h. The mixture was then poured into saturated ammonium chloride and extracted 2×100 mL with ethyl acetate. The organic layer was dried (MgSO$_4$), filtered through silica gel with ethyl acetate and evaporated in vacuo. The crude oil was flash chromatographed to give 3-[[3-(1,1-dimethylethyl)-1-methyl-1H-pyrazol-5-yl]oxy-5-methoxypyridazine (1.14 g, 62% yield) as an oil which solidified upon standing to a white solid.

EXAMPLE 10

This example describes the preparation of 5-methoxy-3-[[2-(tetrahydro-2H-pyran-2-yl)-3-(trifluoromethyl)-1H-pyrazol-5-yl]oxy]pyridazine (Compound No. 36).

A. 3-(Trifluoromethyl)-1H-pyrazol-5-ol (5.0 g, 0.032 mole) which is known in the art and p-toluene-sulfonic acid monohydrate (0.08 g) were dissolved in ethyl acetate (30 mL) and warmed to 50° C. 3,4-Dihydro-2H-pyran (2.9 g, 0.034 mole) was slowly added over a 10 minute period. After stirring 30 minutes at 50° C., the mixture was cooled and diluted with 100 mL of ethyl acetate. This solution was washed twice with 0.5% hydrochloric acid solution, then dried with magnesium sulfate, filtered and concentrated in vacuo. The residue was treated with 5 mL of ethyl acetate and 20 mL hexanes and filtered to give 1-(tetrahydro-2H-pyran-2-yl)-3-(trifluoromethyl)-1H-pyrazol-5-ol (5.8 g, 76% yield) as a white solid, mp=129°–130° C.

Anal. Calc. for C$_9$H$_{11}$N$_2$O$_2$F$_3$:

C, 45.77; H, 4.69; N, 11.86 Found: C, 45.90; H, 4.68; N, 11.84

B. 1-(Tetrahydro-2H-pyran-2-yl)-3-(trifluoromethyl)-1H-pyrazol-5-ol (2.37 g, 0.010 mole), 3-chloro-5-methoxypyridazine (1.39 g, 0.0096 mole), toluene (60 mL), and 2,6 lutidine (1.5 g, 0.014 mole) were heated and held at reflux for 3 hours. The mixture was cooled, diluted with 100 mL of dichloromethane, and washed with 1% hydrochloric acid followed by 1% sodium hydroxide solution. The washed solution was dried over magnesium sulfate, filtered and concentrated in vacuo. The residue was chromatographed on silica gel using ethyl acetate/cyclohexane to give 5-methoxy-3-[[1-(tetrahydro-2H-pyran-2-yl)-3-(trifluoromethyl)-1H-pyrazol-5-yl]oxy]pyridazine (1.96 g, 59% yield) as a white solid.

EXAMPLE 11

This example describes the preparation of 5-methoxy-3-[[3-(trifluoromethyl)-1H-pyrazol-5-yl]oxy]pyridazine (Compound No. 37).

5-Methoxy-3-[[2-(tetrahydro-2H-pyran-2-yl)-3-(trifluoromethyl)-1H-pyrazol-5-yl]oxy]pyridazine (Compound No. 36, 0.75 g (0.0021 mole), 4 drops of 37% hydrochloric acid, and 10 mL of methanol were heated and held at 50° C. for 1 hour. The mixture was cooled, diluted with 30 ml water and neutralized with sodium bicarbonate. Filtration gave 5-methoxy-3-[[3-(trifluoromethyl)-1H-pyrazol-5-yl]oxy]pyridazine (0.36 g, 65% yield) as a white solid.

EXAMPLE 12

This example describes the preparation of 5-[(5-methoxy-3-pyridazinyl)oxy]-1-methyl-1H-pyrazole-3-carboxaldehyde (Compound No. 48).

3-[[3-(Difluoromethyl)-1-methyl-1H-pyrazol-5-yl]oxy]-5-methoxypyridazine (Compound No. 45, 4.5 g, 0.017 mole) and dichloromethane (80 mL) were stirred and cooled with a water bath while aluminum chloride (4.3 g, 0.031 mole, (note: this aluminum chloride was old and wet) was added and the mixture was then stirred at room temperature for 5 hours. The mixture was poured into cold water and the aqueous phase washed three times with dichloromethane. The pH of the aqueous phase was adjusted to 4, using 10% sodium hydroxide; and the product was extracted with ethyl acetate. The extracts were dried with magnesium sulfate, filtered and concentrated in vacuo. The residue was purified by chromatography on silica gel to give 5-[(5-methoxy-3-pyridazinyl)oxy]-1-methyl-1H-pyrazole-3-carboxaldehyde (0.50 g, 12% yield) as white solid.

EXAMPLE 13

This example describes the preparation of 5-methoxy-3-[[1-methyl-4-nitro-3-(trifluoromethyl)-1H-pyrazol-5-yl]oxy]pyridazine (Compound No. 51).

5-Methoxy-3-[[1-methyl-3-(trifluoromethyl)-1H-pyrazol-5-yl]oxy]pyridazine (Compound No. 5, 1.2 g, 0.0043 mole) was added to a mixture of nitric acid (5 mL) and sulfuric acid (13 mL), and the mixture was stirred at room temperature for 18 hours. The reaction mixture was poured into ice and neutralized with 10% sodium hydroxide. Filtration gave, after drying, 5-methoxy-3-[[1-methyl-4-nitro-3-(trifluoromethyl)-1H-pyrazol-5-yl]oxy]pyridazine (1.36 g, 99% yield) as a beige solid.

EXAMPLE 14

This example describes the preparation of 5-[(5-methoxy-3-pyridazinyl)oxy]-1-methyl-3-(trifluoromethyl)-1H-pyrazole-4-carboxaldehyde (Compound No. 54).

A. 1-Methyl-3-(trifluoromethyl)-1H-pyrazol-5-ol (9.8 g, 0.059 mole) was added in portions to a mixture of phosphorus oxychloride (9.2 g, 0.060 mole) and N,N-dimethylformamide (10 mL, 0.12 mole) with cooling to control the reaction temperature near 40° C. The mixture was then heated and held at 90°–100° C. for one hour and poured while still warm (50° C.) into a mixture of methanol and water. The pH was adjusted to basic with 10% sodium hydroxide. The aqueous solution was washed with ether, then adjusted to acidic pH with 37% hydrochloric acid, and extracted with a mixture of ether and ethyl acetate. The extracts were dried with magnesium sulfate, filtered and concentrated in vacuo to give 5-hydroxy-1-methyl-3-(trifluoromethyl)-1H-pyrazole-4-carboxaldehyde (9.4 g, 82% yield) which was recrystallized from ethyl acetate/cyclohexane to give a white solid, mp=116°–118° C.

Anal. Calc. for C$_6$H$_5$N$_2$O$_2$F$_3$:

C, 37.12; H, 2.50; N, 14.43 Found: C, 37.04; H, 2.53; N, 14.32

B. 5-Hydroxy-1-methyl-3-(trifluoromethyl)-1H-pyrazole-4-carboxaldehyde (3.0 g, 0.015 mole), 3-chloro-5-methoxypyridazine (2.3 g, 0.015 mole), 2,6-lutidine (2.8 g, 0.025 mole), and toluene (80 mL) were heated in a flask equipped with a short Vigreux column until 5 mL of solvent had distilled. The mixture was then held at reflux for 4 hours, cooled, poured into 1% hydrochloric acid, and extracted with a mixture of ether and ethyl acetate. The combined extracts were washed with 1% hydrochloric acid, 1% sodium hydroxide, 5% sodium chloride, then dried with magnesium sulfate, filtered and concentrated in vacuo. The residue was purified by silica gel chromatography using ethyl acetate/cyclohexane to give 5-[(5-methoxy-3-pyridazinyl)oxy]-1-methyl-3-(trifluoromethyl)-1H-pyrazole-4-carboxaldehyde (2.53 g, 55% yield) as a yellow solid.

EXAMPLE 15

This example describes the preparation of 3-[(3-ethoxy-1-methyl-1H-pyrazol-5-yl)oxy]-5-methoxypyridazine (Compound No. 72).

A. Methylhydrazine (2.6 g, 0.056 mole) was added to a solution of ethyl 3,3-diethoxyacrylate (10.0 g, 0.053 mole) in ethanol (50 mL) and the mixture was heated and held at reflux for 18 hours. After cooling, water, saturated brine, and 3 mL of concentrated sulfuric acid were added; and the product was extracted with ethyl acetate. The combined extracts were dried with magnesium sulfate, filtered and concentrated in vacuo. Purification by chromatography on silica gel using ethyl acetate/cyclohexane gave 5-ethoxy-2,4-dihydro-2-methyl-3H-pyrazol-3-one (3.2 g, 42% yield) as a white solid, mp=79°–80° C.

Anal. Calc. for $C_6H_{10}N_2O_2$:

C, 50.69; H, 7.09; N, 19.71 Found: C, 50.77; H, 7.09; N, 19.75

B. 5-Ethoxy-2,4-dihydro-2-methyl-3H-pyrazol-3-one (0.63 g, 0.0044 mole), 3-chloro-5-methoxypyridazine (0.64 g, 0.0044 mole), potassium carbonate (1.50 g, 0.010 mole), cuprous bromide (0.05 g, 0.0003 mole) and anhydrous dimethyl sulfoxide (10 mL) were heated and held at 90° C. for 42 hours. The mixture was cooled, treated with 1% hydrochloric acid solution and extracted with ethyl acetate. The combined extracts were washed with 2% sodium hydroxide, dried with magnesium sulfate, filtered and concentrated in vacuo. Purification by chromatography on silica gel using ethyl acetate/cyclohexane gave a tan solid, which was recrystallized from ethyl acetate/methylcyclohexane to give 5-methoxy-3-[(3-ethoxy-1-methyl-1H-pyrazol-5-yl)oxy]pyridazine (0.22 g, 22% yield) as a white solid.

EXAMPLE 16

This example describes the preparation of 3-[[3-[(1,1-dimethylethyl)dimethylsilyl]-1-methyl-1H-pyrazol-5-yl]oxy]-5-methoxypyridazine (Compound No. 44).

A. 2,4-Dihydro-3H-pyrazol-3-one (5 g, 0.060 mole) which is known in the art, t-butyldimethylsilyl chloride (18.84 g, 0.125 mole), triethylamine (20.7 mL, 0.149 mole) and catalytic 4-N,N-dimethylaminopyridine (0.02 g) were refluxed under $N_2$ in methylene chloride (150 mL) for 4 hours. The mixture was then filtered and evaporated in vacuo and then triturated with ethyl acetate, filtered and evaporated in-vacuo again to give a crude oil. This oil was distilled through a short path at 0.1 mm of Hg collecting the product at 91°–92° C. 1-[(1,1-Dimethylethyl)dimethylsilyl]-3-[[1,1-dimethylethyl)dimethylsilyl]oxy]-1H-pyrazole (18.24 g, 98% yield) was obtained as a clear liquid.

Anal. Calc. for $C_{15}H_{32}N_2OSi_2$:

C, 57.63; H, 10.32; N, 8.96 Found: C, 57.72; H, 10.35; N, 8.86

B. 1-[(1,1-Dimethylethyl)dimethylsilyl]-3-[[(1,1-dimethylethyl)dimethylsilyl]oxy]-1H-pyrazole (1.0 g, 0.0032 mole) was stirred at −78° C. under $N_2$ while n-butyllithium (2.21 mL of a 1.6M solution in hexanes, 0.00353 mole) was added dropwise via syringe over 15 minutes. The mixture was then allowed to warm to room temperature and refluxed for 2 hours. The mixture was poured into water and extracted 2×100 mL with ethyl acetate. The organic layer was dried ($MgSO_4$), filtered and evaporated in vacuo to give 3-[(1,1-dimethylethyl)-dimethylsilyl]-5-[[(1,1-dimethylethyl)dimethylsilyl]oxy]-1H-pyrazole (0.9 g, 90% yield) as an oil which was used without further purification. The 3-[(1,1-dimethylethyl)dimethylsilyl]-5-[[(1,1-dimethylethyl)dimethylsilyl]-oxy-1H-pyrazole was then taken up in methylene chloride (15 mL) and refluxed under $N_2$ in the presence of excess methyl iodide (3.2 mL) for 18 hours. The mixture was then poured into ethyl acetate and extracted 2×100 mL with water. The organic layer was dried ($MgSO_4$), filtered and evaporated in vacuo to give 3-[(1,1-dimethylethyl)dimethylsilyl]-1-methyl-1H-pyrazol-5-ol (0.48 g, 78% yield) as an oil which was used in the next step without further purification.

C. 3-[(1,1-Dimethylethyl)dimethylsilyl]-1-methyl-1H-pyrazol-5-ol (0.48 g, 0.0023 mole), 3-chloro-5-methoxypyridazine (0.36 g, 0.00249 mole) and 2,6-lutidine (0.396 mL, 0.003396 moles) were refluxed under $N_2$ in xylene (20 mL) for 18 hours. The mixture was then filtered through silica gel with ethyl acetate and evaporated in vacuo. The crude compound was purified by reverse phase chromatography to give 3-[[3-[(1,1-dimethylethyl)dimethylsilyl]-1-methyl-1H-pyrazol-5-yl]oxy]-5-methoxypyridazine (0.19 g, 26% yield) as a brown solid.

EXAMPLE 17

This example describes the preparation of 5-methoxy-3-[[1-methyl-3-(trifluoromethyl)-1H-pyrazol-5yl]oxy]pyridazine, 1-oxide (Compound No. 55).

5-Methoxy-3-[[1-methyl-3-(trifluoromethyl)-1H-pyrazol-5-yl]oxy]pyridazine (Compound No. 5, 1.0 g, 0.00365 mole) and m-chloroperbenzoic acid (1.3 g, 0.00365 mole of 50% MCPBA) were stirred under $N_2$ at room temperature in chloroform (50 mL) for 18 hours. This mixture was partitioned between 1N NaOH and ethyl acetate. The organic layer was washed with brine, dried ($MgSO_4$), filtered and evaporated in vacuo to give a crude solid which was recrystallized from ethyl acetate/cyclo-hexane to give 5-methoxy-3-[[1-methyl-3-(trifluoro-methyl)-1H-pyrazol-5-yl]oxy]pyridazine, 1-oxide (0.786 g, 74% yield) as a white solid.

EXAMPLE 18

This example describes the preparation of 3-chloro-4-methoxy-6-[[1-methyl-3-(trifluoromethyl)-1H-pyrazol-5-yl]oxy]pyridazine (Compound No. 56).

5-Methoxy-3-[[1-methyl-3-(trifluoromethyl)-1H-pyrazol-5-yl]oxy]pyridazine, 1-oxide (Compound No. 55, 1.0 g, 0.00344 mole) and phosphorus oxychloride (0.6 g, 0.00391 mole) were refluxed under $N_2$ in carbon tetrachloride (40 mL) for 18 hours. The mixture was then partitioned between water and ethyl acetate. The aqueous layer was extracted again with ethyl acetate and the combined organic layers were washed with saturated sodium bicarbonate, brine, filtered through silica gel with ethyl acetate and evaporated in vacuo. The crude solid was recrystallized from ethyl acetate/cyclohexane to give 3-chloro-4-methoxy-6-[[1-methyl-3-(trifluoromethyl)- 1H-pyrazol-5-yl]oxy]pyridazine (0.681 g, 64% yield) as an off-white solid.

EXAMPLE 19

This example describes the preparation of 5-ethenyl-3-[[1-methyl-3-(trifluoromethyl)-1H-pyrazol-5-yl]oxy]pyridazine (Compound No. 69).

A. 5-Methoxy-3-[[1-methyl-3-(trifluoromethyl)-1H-pyrazol-5-yl]oxy]pyridazine (Compound No. 5, 5.0 g, 0.0182 mole) and phosphorus oxybromide (5.7 g, 0.02 mole) were refluxed under $N_2$ in toluene (100 mL) for 3.5 hours. The mixture was poured into ethyl acetate and extracted 2×200 mL with water. The organic layer was then extracted with saturated sodium bicarbonate, brine, dried ($MgSO_4$), filtered and evaporated in vacuo to give a crude oil. The oil was purified by chromatography on silica gel to give 5-bromo-3-[[1-methyl-3-(trifluoromethyl)-1H-pyrazol-5yl]oxy]pyridazine (2.75 g, 47% yield) as a brown solid which was used directly in the following step.

B. 5-Bromo-3-[[1-methyl-3-(trifluoromethyl)-1H-pyrazol-5-yl]oxy]pyridazine (2.0 g, 0.0066 mole), tributylvinyltin (2.3 g, 0.00726 mole) and $Pd(PhCH_2)Cl(Ph_3P)_2$ (0.1 g, 0.000132 mole) were heated at 100° C. in DMF (75 mL) for 1 hour. The mixture was then poured into ethyl acetate and extracted 2×200 mL with aqueous KF, brine, dried ($MgSO_4$), filtered through a pad of silica gel with ethyl acetate and evaporated in vacuo. The crude oil was purified by silica gel chromatography to give 5-ethenyl-3-[[1-methyl-3-(trifluoromethyl)-1H-pyrazol-5-yl]oxy]pyridazine (1.62 g, 91% yield) as an off-white solid.

EXAMPLE 20

This example describes the preparation of 6-[[1-methyl-3-(trifluoromethyl)-1H-pyrazol-5-yl]oxy]-4-pyridazinecarbonitrile (Compound No. 70).

A. 5-Ethenyl-3-[[1-methyl-3-(trifluoromethyl)-1H-pyrazol-5-yl]oxy]pyridazine (Compound No. 69, 0.8 g, 0.00296 mole) and osmium tetroxide (0.037 g, 0.000146 mole) were stirred under $N_2$ at room temperature in dioxane-water (30 mL-10 mL) for 10 minutes. Sodium periodate (1.3 g, 0.00622 mole) was then added in 0.2 g portions over 1 hour. The mixture was stirred under $N_2$ at room temperature for an additional 2.5 hours. The mixture was partitioned between ethyl acetate and water. The water layer was extracted again with ethyl acetate and the combined organic layers were washed with brine, dried ($MgSO_4$), filtered through a pad of silica gel and evaporated in vacuo. The crude 6-[[1-methyl-3-trifluoromethyl)-1H-pyrazol-5-yl]oxy]-4-pyridazinecarboxaldehyde (0.73 g, 91% yield) was used directly in the next step.

B. 6-[[1-Methyl-3-(trifluoromethyl)-1H-pyrazol-5-yl]oxy]-4-pyridazinecarboxaldehyde (0.73 g, 0.00268 mole), hydroxylamine hydrochloride (0.2 g, 0.00295 mole) and sodium hydroxide (1.6 mL of a 2.5N solution, 0.00402 mole) were stirred under $N_2$ at room temperature in ethanol-water (20 mL-6 mL) for 18 hours. The mixture was partitioned between water and ethyl acetate. The aqueous layer was extracted again with ethyl acetate. The combined organic layers were washed with brine, dried ($MgSO_4$), filtered through a pad of silica gel with ethyl acetate and evaporated in vacuo. 6-[[1-Methyl-3-(trifluoromethyl)-1H-pyrazol-5-yl]oxy]-4-pyridazinecarboxaldehyde, oxime (0.52 g, 67% yield) was obtained as an off white solid which was used directly in the next step.

C. 6-[[1-Methyl-3-(trifluoromethyl)-1H-pyrazol-5-yl]oxy]-4-pyridazinecarboxaldehyde, oxime (0.3 g, 0.00104 mole) and phosphorus oxychloride (0.5 g, 0.00326 mole) were refluxed under $N_2$ in chloroform (20 mL) for 18 hours. The mixture was partitioned between water and ethyl acetate. The water layer was extracted again with ethyl acetate. The combined organic layers were washed with brine, dried ($MgSO_4$), filtered through a pad of silica gel and evaporated in vacuo. The crude oil was purified by silica gel chromatography to give 6-[[1-methyl-3-(trifluoromethyl)-1H-pyrazol-5-yl]oxy]-4-pyridazinecarbonitrile (Compound No. 70, 0.235 g, 84% yield) as a yellow brown solid. This compound could be recrystallized from ethyl acetate/cyclohexane to give an off-white solid.

Several other compounds of the present invention were prepared using generally the procedures illustrated above or other procedure obvious to one skilled in the art. Specific compounds illustrated of the present invention are given below where the prepared compounds are structurally depicted and named. Melting points and elemental analyses are provided for these compounds in the following table.

| Compound No. | Name | Structure | Analysis (%) Calc'd | Found |
|---|---|---|---|---|
| 1 | pyridazine,-3-chloro-6-[[4-chloro-1-methyl-5-(trifluoromethyl)-1H-pyrazol-3-yl]-oxy]- MP: 98.0–100.0 | 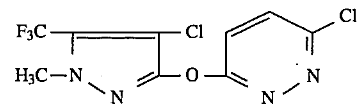 | C 34.53<br>H 1.61<br>Cl 22.65<br>F 18.21<br>N 17.90 | 34.59<br>1.61<br><br><br>17.88 |
| 2 | pyridazine,-3-[[4-chloro-1-methyl-5-(trifluoromethyl)-1H-pyrazol-3-yl]-oxy]-5-methoxy- MP: 94.5–96.5 | 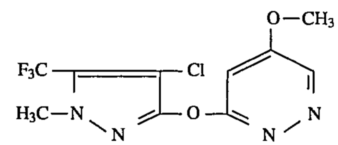 | C 38.91<br>H 2.61<br>Cl 11.49<br>F 18.47<br>N 18.15 | |
| 3 | pyridazine,-3-chloro-6-[[1-methyl-3-(trifluoromethyl)-1H-pyrazol-5-yl]-oxy]- MP: 69.0–71.0 | 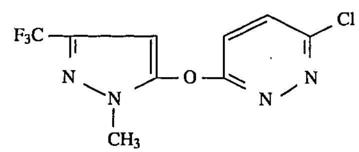 | C 38.80<br>H 2.17<br>Cl 12.72<br>F 20.46<br>N 20.11 | 38.90<br>2.19<br><br><br>20.16 |
| 4 | pyridazine,-3-chloro-6-[[1-methyl-5-(trifluoromethyl)-1H-pyrazol-3-yl]-oxy]- MP: 79.0–82.0 | 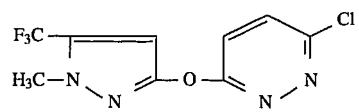 | C 38.80<br>H 2.17<br>Cl 12.72<br>F 20.46<br>N 20.11 | 38.88<br>2.16<br><br><br>20.07 |
| 5 | pyridazine,-5-methoxy-3-[[1-methyl-3-(trifluoromethyl)-1H-pyrazol-5-yl]-oxy]- MP: 100.0–102.0 | 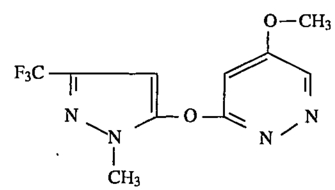 | C 43.80<br>H 3.31<br>F 20.79<br>N 20.43 | 43.96<br>3.34<br><br>20.36 |
| 6 | pyridazine,-5-methoxy-3-[[1-methyl-5-(trifluoromethyl)-1H-pyrazol-3-yl]-oxy]- MP: 80.0–83.0 | 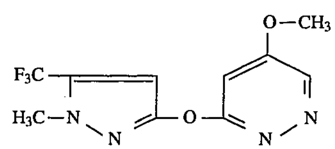 | C 43.80<br>H 3.31<br>F 20.79<br>N 20.43 | 44.01<br>3.25<br><br>20.57 |

-continued

| Compound No. | Name | Structure | Analysis (%) Calc'd | Found |
|---|---|---|---|---|
| 7 | pyridazine,-5-methyl-3-[[1-methyl-3-(trifluoromethyl)-1H-pyrazol-5-yl]-oxy]- MP: 65.0 | 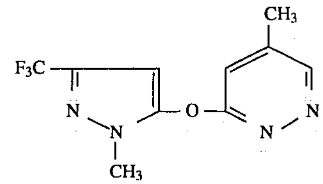 | C 46.52<br>H 3.51<br>F 22.08<br>N 21.70 | 46.40<br>3.56<br>—<br>21.49 |
| 8 | pyridazine,-4-methyl-3-[[1-methyl-3-(trifluoromethyl)-1H-pyrazol-5-yl]-oxy]- MP: 109.0 | 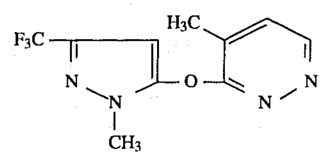 | C 46.52<br>H 3.51<br>F 22.08<br>N 21.70 | 46.62<br>3.52<br>—<br>21.64 |
| 9 | pyridazine, 5-(methylthio)-3-[[1-methyl-3-(trifluoromethyl)-1H-pyrazol-5-yl]-oxy]- MP: 94.0–95.0 | 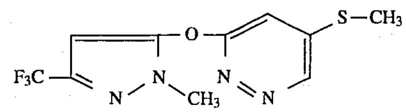 | C 41.38<br>H 3.13<br>F 19.64<br>N 19.30<br>S 11.05 | 41.45<br>3.16<br>—<br>19.40<br>— |
| 10 | 4-pyridazinamine,- N-methyl-6-[[1-methyl-3-(trifluoromethyl)-1H-pyrazol-5-yl]-oxy]- MP: 126.0–128.0 | 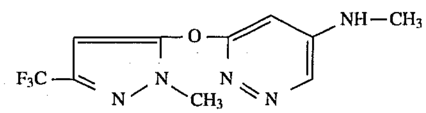 | C 43.96<br>H 3.69<br>F 20.86<br>N 25.63 | 44.75<br>3.77<br>—<br>25.39 |
| 11 | pyridazine, 3,-5-bis[[1-methyl-3-(trifluoromethyl)-1H-pyrazol-5-yl]-oxy]- MP: 115.0–117.0 | 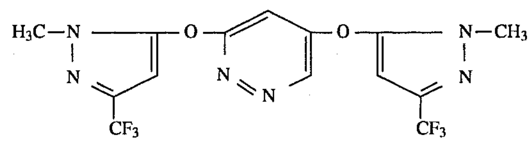 | C 41.19<br>H 2.47<br>F 27.92<br>N 20.58 | 41.39<br>2.51<br>—<br>20.67 |
| 12 | 4-pyridazinol,- 6-[[1-methyl-3-(trifluoromethyl)-1H-pyrazol-5-yl]-oxy]- MP: 203.0–205.0 | 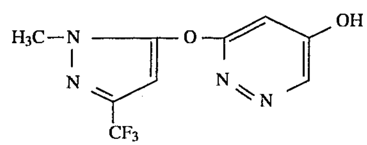 | C 41.55<br>H 2.71<br>F 21.91<br>N 21.53 | 41.83<br>2.72<br>—<br>21.58 |
| 13 | pyridazine,-5-(difluoromethoxy)-3-[[1-methyl-3-(trifluoromethyl)-1H-pyrazol-5-yl]-oxy]- MP: 86.0–88.0 | 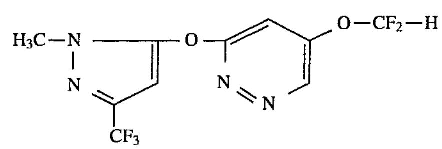 | C 38.72<br>H 2.27<br>F 30.63<br>N 18.06 | 38.75<br>2.26<br>—<br>18.02 |

-continued

| Compound No. | Name | Structure | Analysis (%) Calc'd | Found |
|---|---|---|---|---|
| 14 | pyridazine,- 5-ethoxy-3-[[1-methyl-3-(trifluoromethyl)-1H-pyrazol-5-yl]-oxy]- MP: 97.0–99.0 | 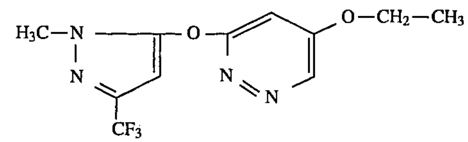 | C 45.84<br>H 3.85<br>F 19.78<br>N 19.44 | 46.03<br>3.86<br><br>19.34 |
| 15 | pyridazine,- 5-methoxy-3-[[1-(phenylmethyl)-3-(trifluoromethyl)-1H-pyrazol-5-yl]-oxy]- MP: | 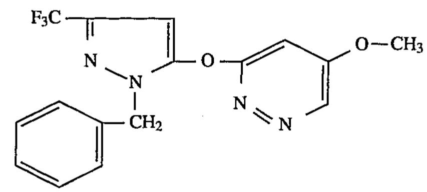 | C 54.86<br>H 3.74<br>F 16.27<br>N 15.99 | 54.69<br>3.78<br><br>15.68 |
| 16 | pyridazine, 5-methoxy-3-[(1-methyl-3-propyl-1H-pyrazol-5-yl)-oxy]- MP: 67.0–69.0 | 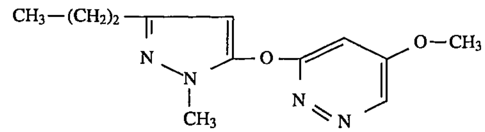 | C 58.05<br>H 6.50<br>N 22.57 | 58.13<br>6.52<br>22.51 |
| 17 | pyridazine,- 3-[[3-(1,-1-dimethylethyl)-1-methyl-1H-pyrazol-5-yl]-oxy]-5-methoxy- MP: 88.8–90.3 | 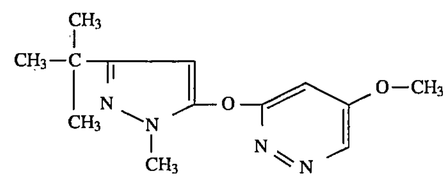 | C 59.53<br>H 6.92<br>N 21.36 | 59.74<br>6.95 |
| 18 | pyridazine,- 5-methoxy-3-[[1-methyl-3-(pentafluoroethyl)-1H-pyrazol-5-yl]-oxy]- MP: 65.0–66.0 | 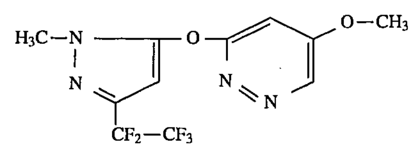 | C 40.75<br>H 2.80<br>F 29.30<br>N 17.28 | 41.00<br>2.90<br><br>17.09 |
| 19 | pyridazine,- 3-[[3-(heptafluoropropyl)-1-methyl-1H-pyrazol-5-yl]-oxy]-5-methoxy- MP: 86.2–88.0 | 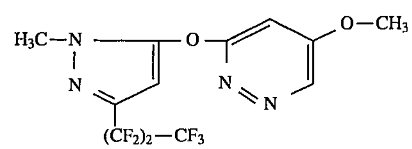 | C 38.51<br>H 2.42<br>f 35.54<br>N 14.97 | 38.69<br>2.47 |

-continued

| Compound No. | Name | Structure | Analysis (%) Calc'd | Found |
|---|---|---|---|---|
| 20 | pyridazine,-3-[(1,-3-dimethyl-1H-pyrazol-5-yl)-oxy]-5-methoxy- MP: 90.0–93.0 | 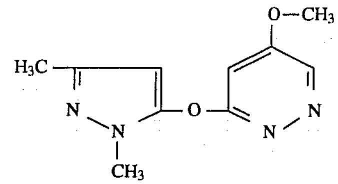 | C 54.54<br>H 5.49<br>N 25.44 | 53.37<br>5.66<br>24.90 |
| 21 | pyridazine,- 3-[[3-(difluoromethyl)-1-methyl-1H-pyrazol-5-yl]-oxy]-5-methoxy- MP: 124.0–125.0 | 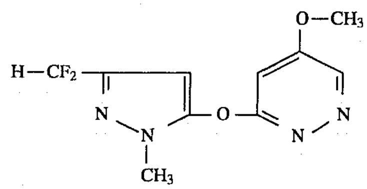 | C 46.88<br>H 3.93<br>F 14.83<br>N 21.87 | 46.98<br>3.95<br>21.81 |
| 22 | pyridazine,- 3-[[4-chloro-1-methyl-3-(trifluoromethyl)-1H-pyrazol-5-yl]-oxy]-5-methoxy- MP: 104.0–106.0 | 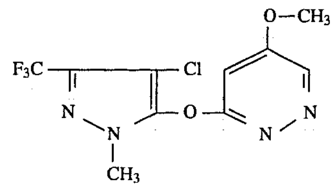 | C 38.91<br>H 2.61<br>Cl 11.49<br>F 18.47<br>N 18.15 | 39.05<br>2.62<br>18.11 |
| 23 | pyridazine,- 5-methoxy-3-[[1-(2,-2,-2-trifluoroethyl)-3-(trifluoromethyl)-1H-pyrazol-5-yl]-oxy]- MP: 74.0–76.0 | 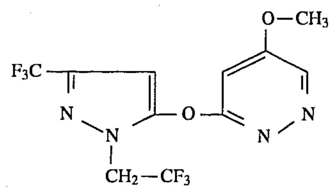 | C 38.61<br>H 2.36<br>F 33.31<br>N 16.37 | 38.60<br>2.37<br>16.27 |
| 24 | pyridazine,- 5-methoxy-3-[[1-propyl-3-(trifluoromethyl)-1H-pyrazol-5-yl]-oxy]- MP: | 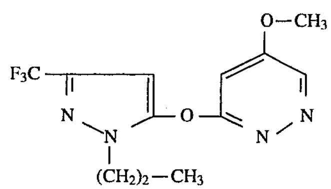 | C 47.68<br>H 4.34<br>F 18.86<br>N 18.54 | 47.76<br>4.38<br>18.47 |

-continued

| Compound No. | Name | Structure | Analysis (%) Calc'd | Found |
|---|---|---|---|---|
| 25 | pyridazine,-3-[[4-fluoro-1-methyl-3-(trifluoromethyl)-1H-pyrazol-5-yl]-oxy]-5-methoxy-<br>MP: 97.0–99.0 | 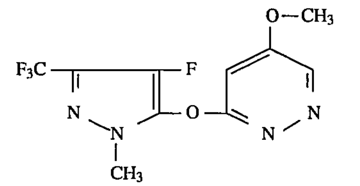 | C 41.11<br>H 2.76<br>F 26.01<br>N 19.17 | 41.33<br>2.74<br>19.22 |
| 26 | 1H-pyrazole-3-carboxylic acid,-1-methyl-5-(5-methoxy-3-pyridazinyl)-,-methyl ester<br>MP: | 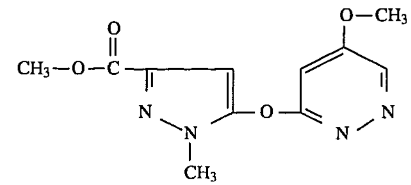 | C 50.00<br>H 4.58<br>N 21.20 | 50.11<br>4.60<br>21.15 |
| 27 | pyridazine,-5-methoxy-3-[(1-methyl-1H-pyrazol-5-yl)-oxy]-<br>MP: 127.0–129.0 | 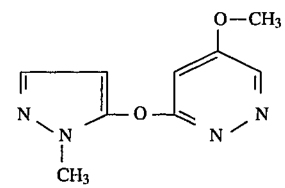 | C 52.42<br>H 4.89<br>N 27.17 | 52.43<br>4.91<br>27.01 |
| 28 | pyridazine,-3-[[4-chloro-1-methyl-5-(methylthio)-1H-pyrazol-3-yl]-oxy]-5-methoxy-<br>MP: 102.0–103.0 | 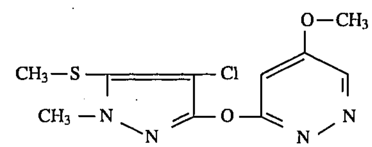 | C 41.89<br>H 3.87<br>Cl 12.36<br>N 19.54<br>S 11.18 | 41.98<br>3.87<br>19.61 |
| 29 | pyridazine,-3-[[4-chloro-5-(difluoromethyl)-1-methyl-1H-pyrazol-3-yl]-oxy]-5-methoxy-<br>MP: 123.0–124.0 | 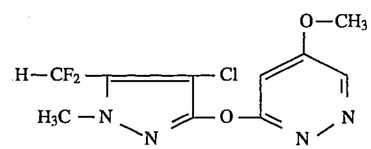 | C 41.32<br>H 3.12<br>Cl 12.20<br>F 13.07<br>N 19.28 | 41.30<br>3.11<br>19.21 |
| 30 | pyridazine,-3-[[4-chloro-1-methyl-5-(methylsulfonyl)-1H-pyrazol-3-yl]-oxyl]-5-methoxy-, 1-oxide<br>MP: 168.0–170.0 | 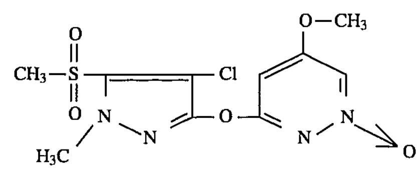 | C 35.88<br>H 3.31<br>Cl 10.59<br>N 16.74<br>S 9.58 | 36.18<br>3.32<br>16.75 |

-continued

| Compound No. | Name | Structure | Analysis (%) Calc'd | Found |
|---|---|---|---|---|
| 31 | pyridazine,- 3-[(4,-5-dichloro-1-methyl-1H-pyrazol-3-yl)-oxy]-5-methoxy- MP: 122.0–124.0 | 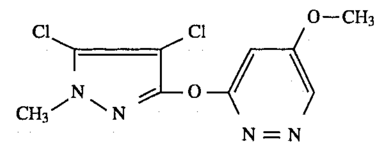 | C 39.30<br>H 2.93<br>Cl 25.78<br>N 20.37 | 39.29<br>2.96<br>20.27 |
| 32 | pyridazine,- 3-[[5-(difluoromethyl)-1-methyl-1H-pyrazol-3-yl]-oxy]-5-methoxy- MP: 104.0–105.0 | 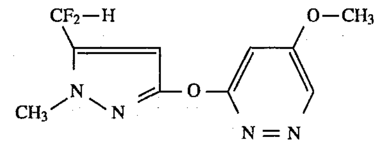 | C 46.88<br>H 3.93<br>F 14.83<br>N 21.87 | 47.10<br>3.95<br>21.79 |
| 33 | pyridazine,- 5-methoxy-3-[[1-methyl-3-(1-methylethyl)-1H-pyrazol-5-yl]-oxy]- MP: 53.0–56.0 | 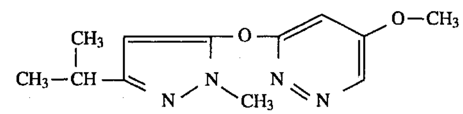 | C 58.05<br>H 6.50<br>N 22.57 | 58.01<br>6.50<br>22.64 |
| 34 | pyridazine,- 3-[[3-(chlorodifluoromethyl)-1-methyl-1H-pyrazol-5-yl]-oxy]-5-methoxy- MP: 103.0–104.0 | 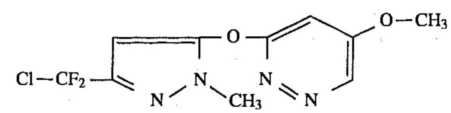 | C 41.32<br>H 3.12<br>Cl 12.20<br>F 13.07<br>N 19.28 | 41.59<br>3.17<br>19.35 |
| 35 | pyridazine,- 5-methoxy-3-[(1-methyl-3-phenyl-1H-pyrazol-5-yl)-oxy]- MP: 114.0–116.0 | 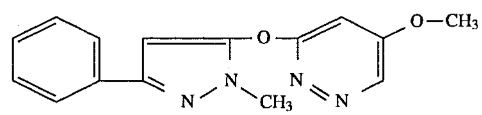 | C 63.82<br>H 5.00<br>N 19.85 | 64.10<br>5.05<br>20.00 |
| 36 | pyridazine,- 5-methoxy-3-[[1-(tetrahydro-2H-pyran-2-yl)-3-(trifluoromethyl)-1H-pyrazol-5-yl]-oxy]- MP: 77.0–79.0 | 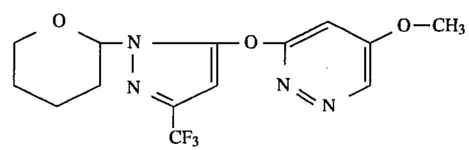 | C 48.84<br>H 4.39<br>F 16.56<br>N 16.27 | 48.92<br>4.38 |
| 37 | pyridazine,- 5-methoxy-3-[[3-(trifluoromethyl)-1H-pyrazol-5-yl]-oxy]- MP: 164.0–166.0 | 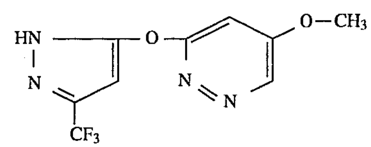 | C 41.55<br>H 2.71<br>F 21.91<br>N 21.53 | 41.72<br>2.70 |

-continued

| Compound No. | Name | Structure | Analysis (%) | |
|---|---|---|---|---|
| | | | Calc'd | Found |
| 38 | pyridazine,-3-[[1-ethyl-3-(trifluoromethyl)-1H-pyrazol-5-yl]oxy]-5-methoxy- MP: 82.0–84.0 | 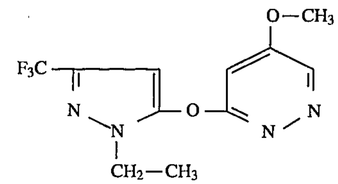 | C 45.84<br>H 3.85<br>F 19.78<br>N 19.44 | 46.01<br>3.86 |
| 39 | pyridazine,-2-[[3-(1,1-dimethylpropyl)-1-methyl-1H-pyrazol-5-yl]-oxy]-5-methoxy- MP: 88.0–90.0 | 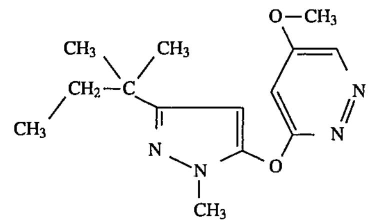 | C 60.85<br>H 7.30<br>N 20.27 | 61.12<br>7.29 |
| 40 | pyridazine,-3-[[3-(2,2-dimethylpropyl)-1-methyl-1H-pyrazol-5-yl]-oxy]-5-methoxy- MP: 72.0–74.0 | 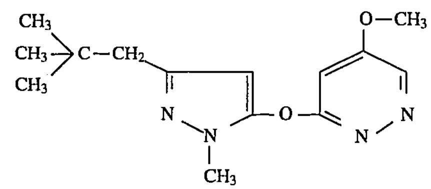 | C 60.85<br>H 7.30<br>N 20.27 | 60.78<br>7.12 |
| 41 | pyridazine,- 5-methoxy-3-[(1-methyl-3-octyl-1H-pyrazol-5-yl])-oxy]- MP: 48.0–50.0 | 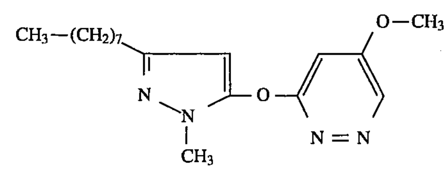 | C 64.12<br>H 8.23<br>N 17.60 | 64.21<br>8.23 |
| 42 | pyridazine,- 5-methoxy-3-[[1-methyl-3-(2-phenylethyl)-1H-pyrazol-5-yl]-oxy]- MP: 88.0–91.0 | 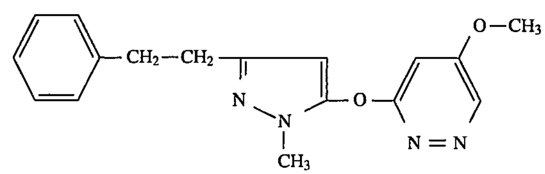 | C 65.79<br>H 5.85<br>N 18.05 | 66.02<br>5.85 |

-continued

| Compound No. | Name | Structure | Analysis (%) Calc'd | Found |
|---|---|---|---|---|
| 43 | pyridazine,-3-[[1-ethyl-3-(pentafluoroethyl)-1H-pyrazol-5-yl]-oxy]-5-methoxy- MP: 63.0–65.0 | 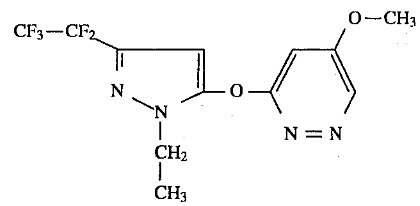 | C 42.61<br>H 3.28<br>F 28.09<br>N 16.56 | 42.55<br>3.33<br><br>16.56 |
| 44 | pyridazine,-3-[[3-((1,1-dimethylethyl)dimethylsilyl]-1-methyl-1H-pyrazol-5-yl]-oxy]-5-methoxy- MP: 90.4–91.4 | 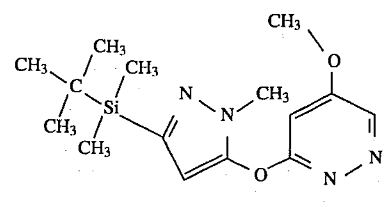 | C 56.22<br>H 7.55<br>N 17.48<br>Si 8.77 | 56.32<br>7.55<br>17.53 |
| 45 | pyridazine,-3-[[3-(dichloromethyl)-1-methyl-1H-pyrazol-5-yl]-oxy]-5-methoxy- MP: 170.0–174.0 | 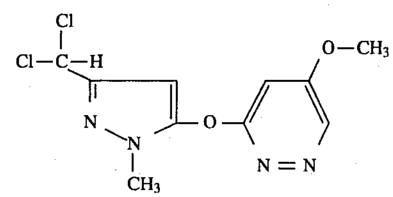 | C 41.54<br>H 3.49<br>Cl 24.52<br>N 19.38 | 41.66<br>3.50 |
| 46 | pyridazine,-5-methoxy-3-[[1-(1-methylethyl)-3-(trifluoromethyl)-1H-pyrazol-5-yl]-oxy]- MP: 62.0–64.0 | 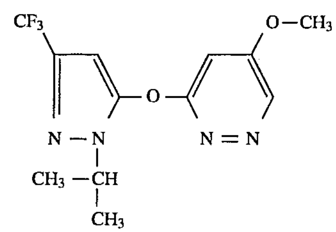 | C 47.68<br>H 4.34<br>F 18.86<br>N 18.54 | 47.72<br>4.32 |
| 47 | pyridazine,-3-[[4-bromo-1-methyl-3-(trifluoromethyl)-1H-pyrazol-5-yl]-oxy]-5-methoxy- MP: 103.0–106.0 | 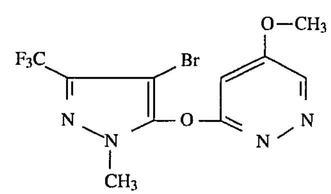 | C 34.01<br>H 2.28<br>Br 22.63<br>F 16.14<br>N 15.87 | 34.31<br>2.47 |

-continued

| Compound No. | Name | Structure | Analysis (%) Calc'd | Found |
|---|---|---|---|---|
| 48 | 1H-pyrazole-3-carboxaldehyde,- 5-[(5-methoxy-3-pyridazinyl)-oxy]-1-methyl- MP: 142.0–143.0 | 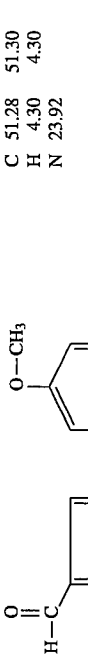 | C 51.28<br>H 4.30<br>N 23.92 | 51.30<br>4.30 |
| 49 | pyridazine,- 3-[[3-(dimethoxymethyl)-1-methyl-1H-pyrazol-5-yl]-oxy]-5-methoxy- MP: 99.0–101.0 | 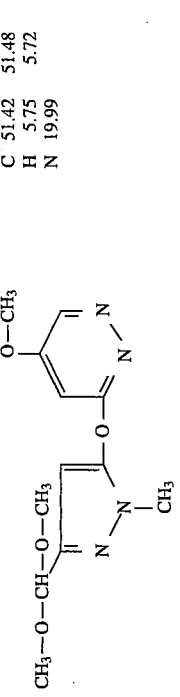 | C 51.42<br>H 5.75<br>N 19.99 | 51.48<br>5.72 |
| 50 | pyridazine,- 5-methoxy-4-methyl-3-[[1-methyl-3-(trifluoromethyl)-1H-pyrazol-5-yl]-oxy]- MP: 95.0–97.0 | 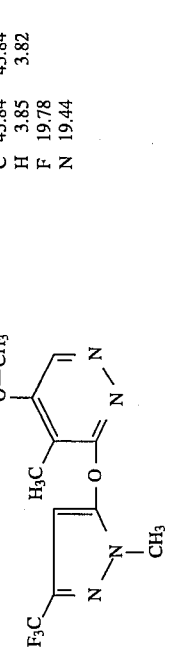 | C 45.84<br>H 3.85<br>F 19.78<br>N 19.44 | 45.84<br>3.82 |
| 51 | pyridazine,- 5-methoxy-4-nitro-3-[[1-methyl-3-(trifluoromethyl)-1H-pyrazol-5-yl]-oxy]- MP: 147.0–149.0 | 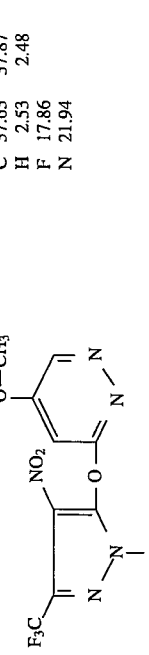 | C 37.63<br>H 2.53<br>F 17.86<br>N 21.94 | 37.87<br>2.48 |
| 52 | pyridazine,- 5-methoxy-3-[[1-phenyl-3-(trifluoromethyl)-1H-pyrazol-5-yl]-oxy]- MP: | 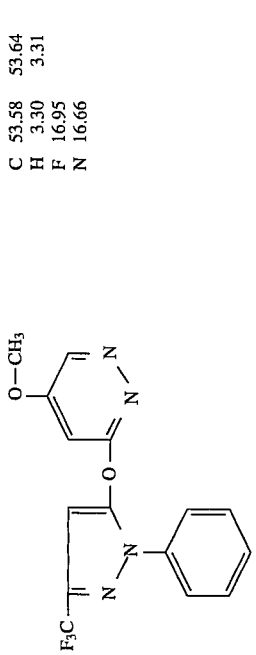 | C 53.58<br>H 3.30<br>F 16.95<br>N 16.66 | 53.64<br>3.31 |

-continued

| Compound No. | Name | Structure | Analysis (%) | |
|---|---|---|---|---|
| | | | Calc'd | Found |
| 53 | pyridazine,-3-[[1,4-dimethyl-3-(trifluoromethyl)-1H-pyrazol-5-yl]-oxy]-5-methoxy-<br>MP: 145.0–146.0 | 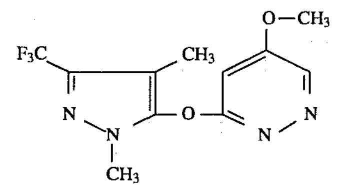 | C 45.84<br>H 3.85<br>F 19.78<br>N 19.44 | 46.00<br>3.88<br><br>19.44 |
| 54 | 1H-pyrazole-4-carboxaldehyde,-5-[(5-methoxy-3-pyridazinyl)-oxy]-1-methyl-3-(trifluoromethyl)-<br>MP: 113.0–115.0 | 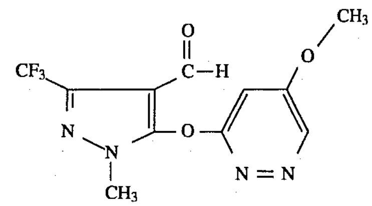 | C 43.72<br>H 3.00<br>F 18.86<br>N 18.54 | 43.98<br>3.04<br><br>18.54 |
| 55 | pyridazine,- 5-methoxy-3-[[1-methyl-3-(trifluoromethyl)-1H-pyrazol-5-yl]-oxy]-,-1-oxide<br>MP: 130.0–132.0 | 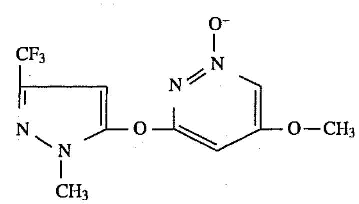 | C 41.39<br>H 3.13<br>F 19.64<br>N 19.31 | 41.50<br>3.18<br><br>19.29 |
| 56 | pyridazine,-3-chloro-4-methoxy-6-[[1-methyl-3-(trifluoromethyl)-1H-pyrazol-5-yl]-oxy]-<br>MP: 114.0–117.0 | 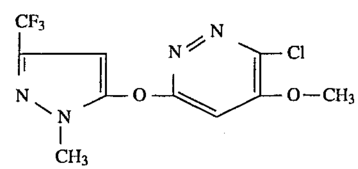 | C 38.91<br>H 2.61<br>Cl 11.49<br>F 18.47<br>N 18.15 | 38.85<br>2.60<br><br>18.22 |
| 57 | 1H-pyrazole-4-carboxylic acid,-3-methoxy-5-[(5-methoxy-3-pyrodazinyl)-oxy]-1-methyl-,-ethyl ester<br>MP: 140.0–143.0 | 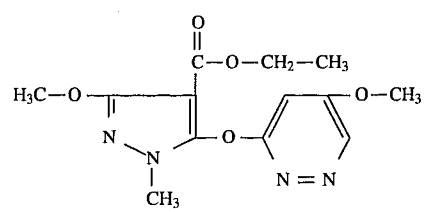 | C 50.65<br>H 5.23<br>N 18.17 | 50.73<br>5.20 |

-continued

| Compound No. | Name | Structure | Analysis (%) Calc'd | Analysis (%) Found |
|---|---|---|---|---|
| 58 | 1H-pyrazole-4-carboxaldehyde,- 5-[(5-methoxy-3-pyridazinyl)-oxy]-1-methyl-3-(trifluoromethyl)-,- methylhydrazone MP: 152.0–155.0 | 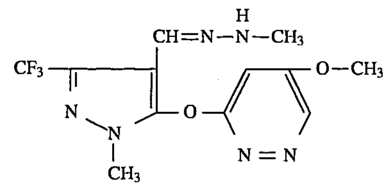 | C 43.64<br>H 3.97<br>F 17.26<br>N 25.45 | 43.92<br>4.00 |
| 59 | 1H-pyrazole-4-carbonitrile,- 5-[(5-methoxy-3-pyridazinyl)-oxy]-1-methyl-3-(trifluoromethyl)- MP: 115.0–117.0 | 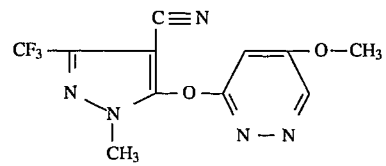 | C 44.16<br>H 2.70<br>F 19.05<br>N 23.41 | 44.40<br>2.89 |
| 60 | 1H-pyrazole-4-carboxylic acid,- 3-ethoxy-5-[(5-methoxy-3-pyridazinyl)-oxy]-1-methyl-,- ethyl ester MP: 126.0–128.0 | 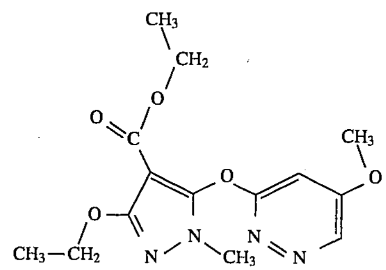 | C 52.17<br>H 5.63<br>N 17.38 | 52.25<br>5.60 |
| 61 | 1H-pyrazol-4-amine,- 2-[(5-methoxy-3-pyridazinyl)-oxy]-1-methyl-5-(trifluoromethyl)- MP: 101.0–103.0 | 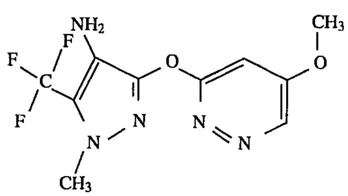 | C 41.53<br>H 3.49<br>F 19.71<br>N 24.21 | 41.62<br>3.46 |
| 62 | 1H-pyrazole-3-carboxylic acid,- 5-[(5-methoxy-3-pyridazinyl)-oxy]-1-methyl- MP: 174.0–175.0 | 1.0 H2O | C 48.00<br>H 4.03<br>N 22.39 | 44.82<br>4.49<br>20.95 |

-continued

| Compound No. | Name | Structure | Analysis (%) | |
|---|---|---|---|---|
| | | | Calc'd | Found |
| 63 | 1H-pyrazole-3-carboxamide,-5-[(5-methoxy-3-pyridazinyl)-oxy]-N,-1-dimethyl-<br>MP: 170.0–172.0 | 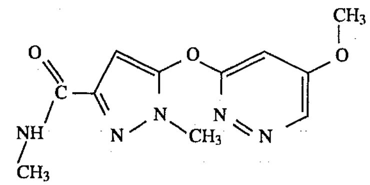 | C 50.19<br>H 4.98<br>N 26.60 | 50.25<br>5.01<br>26.69 |
| 64 | 1H-pyrazole-3-carboxamide,-5-[(5-methoxy-3-pyridazinyl)-oxy]-1-methyl-N-(1-methylethyl)-<br>MP: 122.0–123.0 | 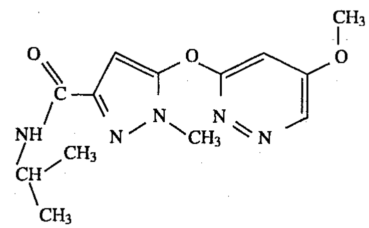 | C 53.60<br>H 5.88<br>N 24.04 | 53.57<br>5.85<br>23.97 |
| 65 | 1H-pyrazole-3-carboxamide,- N-ethyl-5-[-(5-methoxy-3-pyridazinyl)-oxy]-1-methyl-<br>MP: 136.0–137.0 | 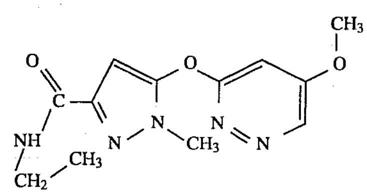 | C 51.98<br>H 5.45<br>N 25.26 | 52.08<br>5.47<br>25.34 |
| 66 | 1H-pyrazole-3-carboxamide,-5-[(5-methoxy-3-pyridazinyl)-oxy]-N,-N,-1-trimethyl-<br>MP: 89.0–90.0 | 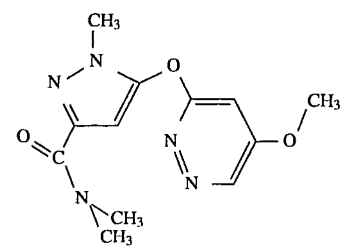 | C 51.98<br>H 5.45<br>N 25.26 | 51.84<br>5.41<br>25.15 |

-continued

| Compound No. | Name | Structure | Analysis (%) | |
|---|---|---|---|---|
| | | | Calc'd | Found |
| 67 | 1H-pyrazole-3-carboxamide,- 5-[(5-methoxy-3-pyridazinyl)-oxy]-1-methyl- MP: 210.0–215.0 | 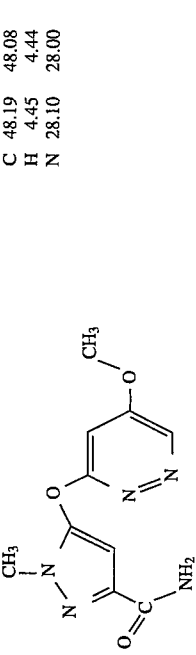 | C 48.19<br>H 4.45<br>N 28.10 | 48.08<br>4.44<br>28.00 |
| 68 | 1H-pyrazole-3-carboxamide,- 5-[(5-methoxy-3-pyridazinyl)-oxy]-1-methyl-N-phenyl- MP: 180.0–182.0 | 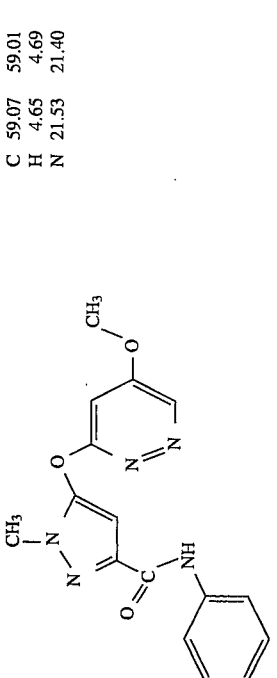 | C 59.07<br>H 4.65<br>N 21.53 | 59.01<br>4.69<br>21.40 |
| 69 | pyridazine,- 5-ethenyl-3-[[1-methyl-3-(trifluoromethyl)-1H-pyrazol-5-yl]-oxy]- MP: 50.0–52.0 | 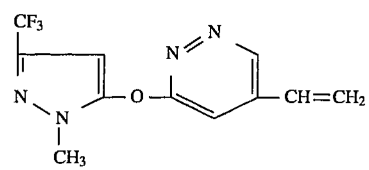 | C 48.89<br>H 3.36<br>F 21.09<br>N 20.73 | 48.95<br>3.38<br>21.09<br>20.65 |
| 70 | 4-pyridazinecarbonitrile,- 6-[[1-methyl-3-(trifluoromethyl)-1H-pyrazol-5-yl]-oxy]- MP: 105.0–107.0 | 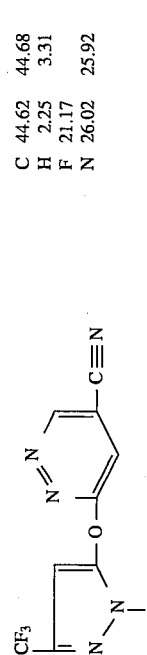 | C 44.62<br>H 2.25<br>F 21.17<br>N 26.02 | 44.68<br>3.31<br>21.17<br>25.92 |
| 71 | pyridazine,- 5-methyl-3-[[1-methyl-3-(trifluoromethyl)-1H-pyrazol-5-yl]-oxy]-,1-oxide MP: 111.0–113.0 | 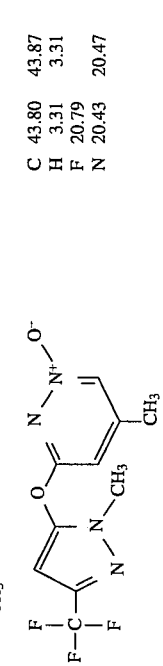 | C 43.80<br>H 3.31<br>F 20.79<br>N 20.43 | 43.87<br>3.31<br>20.79<br>20.47 |

-continued

| Compound No. | Name | Structure | Analysis (%) Calc'd | Found |
|---|---|---|---|---|
| 72 | pyridazine,- 3-[(3-ethoxy-1-methyl-1H-pyrazol-5-yl)-oxy]-5-methoxy- MP: 89.0–90.0 | 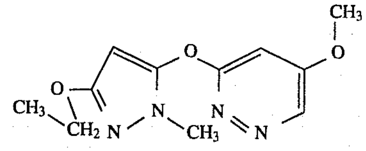 | C 52.79<br>H 5.64<br>N 22.39 | 52.98<br>5.65 |
| 73 | pyridazine,- 5-methoxy-3-[(3-methoxy-1-methyl-1H-pyrazol-5-yl)-oxy]- MP: 89.0–92.0 | 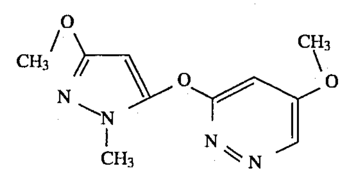 | C 50.84<br>H 5.12<br>N 23.72 | 50.94<br>5.14 |
| 74 | PYRIDAZINE, 5-METHOXY-3-[[1-METHYL-3-[2-(PENTAFLUOROETHYL)-1,3-DIOXOLAN-2-YL]-1H-PYRAZOL-5-YL]OXY]- MP: 110.0–112.0 | 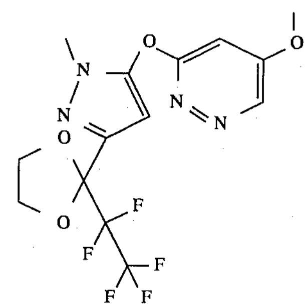 | C 42.43<br>H 3.31<br>N 14.14 | 42.77<br>3.35<br>13.75 |
| 75 | 1H-PUYRAZOLE-3-CARBOXYLIC ACID, 5-[[5-METHOXY-3-PYRIDAZINYL]OXY]-1-METHYL,¦ETHYL ESTER MP: 123.0–124.0 | 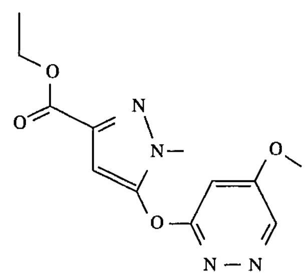 | C 51.80<br>H 5.07<br>N 20.13 | 51.83<br>5.06<br>20.09 |

-continued

| Compound No. | Name | Structure | Analysis (%) Calc'd | Found |
|---|---|---|---|---|
| 76 | 1-HEPTANONE, 2,2,3,3,4,4,5,5,6,6,7,7,7-TRIDECAFLUORO-1-[5-[(5-METHOXY-3-PYRIDAZINYL)OXY]-1-METHYL-1H-PYRAZOL-3-YL]- MP: 132.0–133.0 | 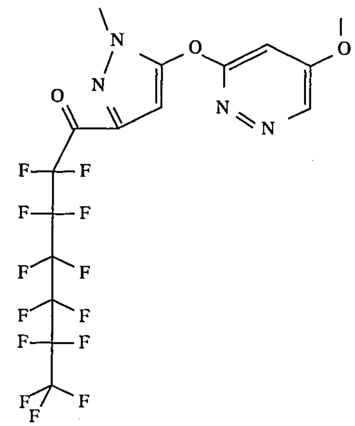 | C 34.80<br>H 1.64<br>N 10.15 | 34.87<br>1.65<br>10.03 |
| 77 | PYRIDAZINE, 5-METHOXY-3-[[1-METHYL-3-(2,2,2-TRIFLUORO-1-METHOXY-METHYL)-1H-PYRAZOL-5-YL]OXY]- MP: 83.0–84.0 | 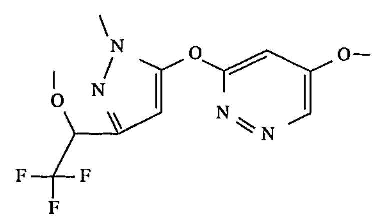 | C 45.29<br>H 4.12<br>N 17.60 | 45.35<br>4.12<br>17.56 |
| 78 | ETHANONE, 2,2,2-TRIFLUORO-1-[5-[(5-METHOXY-3-PYRIDAZINYL)OXY]-1-METHYL-1H-PYRAZOL-3-YL]- MP: 114.0–116.0 | 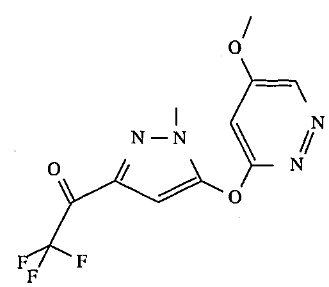 | C 43.72<br>H 3.00<br>N 18.54 | 43.78<br>3.03<br>18.50 |

-continued

| Compound No. | Name | Structure | Analysis (%) Calc'd | Found |
|---|---|---|---|---|
| 79 | PYRIDAZINE, 5-METHOXY-3-[[1-METHYL-3-(1,1,2,2-TETRAFLUOROETHYL)-1H-PYRAZOL-5-YL]OXY]- MP: 132.5–134.0 | 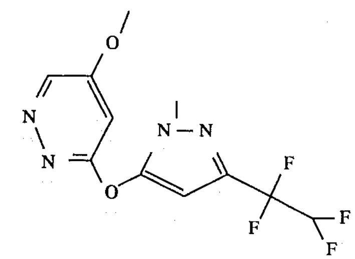 | C 43.15<br>H 3.29<br>N 18.30 | 43.22<br>3.31<br>18.25 |
| 80 | PYRIDAZINE, 5-METHOXY-3-[[1-METHYL-3-(1,2,2,2-TETRAFLUOROETHYL)-1H-PYRAZOL-5-YL]OXY]- MP: 73.0–75.0 | 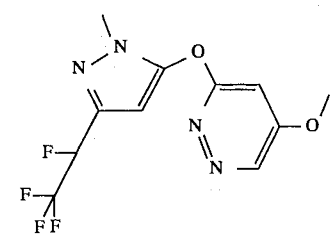 | C 43.15<br>H 3.29<br>N 18.30 | 43.25<br>3.31<br>18.26 |
| 81 | PYRIDAZINE, 5-METHOXY-3-[[1-METHYL-3-(TRIFLUOROETHENYL)1-H-PYRAZOL-5-YL]OXY]- MP: 109.0–112.0 | 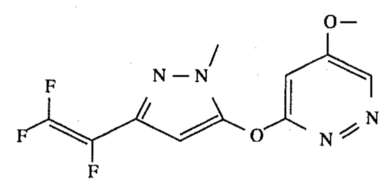 | C 46.16<br>H 3.17<br>N 19.58 | 46.29<br>3.35<br>19.05 |
| 82 | PYRIDAZINE, 3-[[3-(1,1-DIFLUOROETHYL)-1-METHYL-1H-PYRAZOL-5-YL]OXY]-5-METHOXY- MP: 102.0–104.0 | 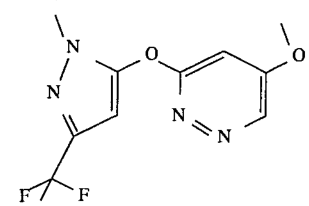 | C 48.89<br>H 4.48<br>N 20.73 | 49.00<br>4.51<br>20.70 |
| 83 | 1H-PYRAZOLE-3-METHANOL, 5-[(5-METHOXY-3-PYRIDAZINYL)OXY]-ALPHA,ALPHA,1-TRIMETHYL- MP: 136.0–137.0 | 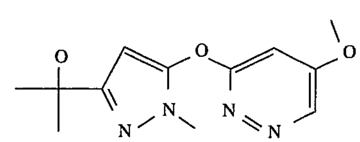 | C 54.54<br>H 6.10<br>N 21.20 | 54.43<br>6.08<br>21.14 |

-continued

| Compound No. | Name | Structure | Analysis (%) Calc'd | Found |
|---|---|---|---|---|
| 84 | PYRIDAZINE, 5-METHOXY-3-[[1-METHYL-3-(PHENYLMETHOXY)]-1-H-PYRAZOL-5-YL]OXY]- MP: 107.0–109.0 | 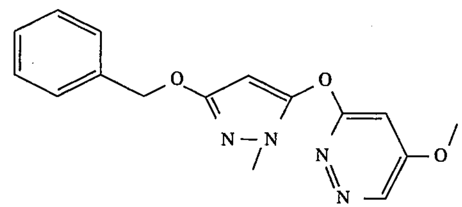 | C 61.53<br>H 5.16<br>N 17.94 | 61.54<br>5.18<br>17.93 |
| 85 | PYRIDAZINE, 3-[[3-(DIFLUOROMETHOXY)-1-METHYL-1H-PYRAZOL-5-YL]OXY]-5-METHOXY- MP: 91.0–93.0 | 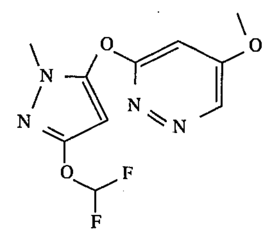 | C 44.12<br>H 3.70<br>N 20.58 | 44.28<br>3.72<br>20.62 |
| 86 | ETHANONE, 1-[5-[(5-METHOXY-3-PYRIDAZINYL)OXY]-1-METHYL-1H-PYRAZOL-3-YL]- MP: 148.0–150.0 | 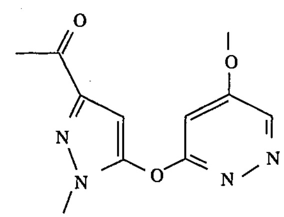 | C 53.22<br>H 4.87<br>N 22.57 | 53.08<br>4.91<br>22.53 |
| 87 | 1H-PYRAZOLE-3-METHANOL, 5-[(5-METHOXY-3-PYRIDAZINYL)OXY]-ALPHA,1-DIMETHYL- MP: 119.0–121.0 | 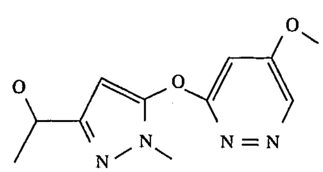 | C 52.79<br>H 5.64<br>N 22.39 | 52.81<br>5.62<br>22.29 |

-continued

| Compound No. | Name | Structure | Analysis (%) Calc'd | Found |
|---|---|---|---|---|
| 88 | PYRIDAZINE, 5-METHOXY-3-[[1-METHYL-3-(1-METHYLETHENYL)-1H-PYRAZOL-5-YL]OXY]- MP: 90.0–92.0 | 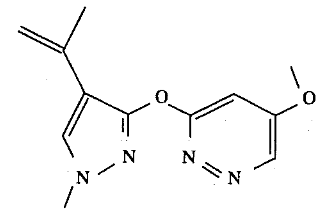 | C 58.53<br>H 5.73<br>N 22.75 | 58.45<br>5.76<br>22.72 |
| 89 | PYRIDAZINE, 5-METHOXY-3-[[3-(1-METHOXY-1-METHYLETHYL)-1-METHYL-1H-PYRAZOL-5-YL]OXY]- MP: 81.0–84.0 | 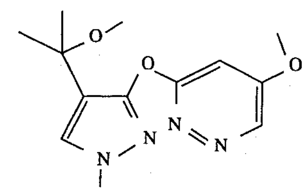 | C 56.10<br>H 6.52<br>N 20.13 | 55.85<br>6.51<br>20.03 |
| 90 | 1H-PYRAZOLE-3-METHANOL, 5-[(5-METHOXY-3-PYRIDAZINYL)OXY]-1-METHYL- MP: 190.0–193.0 | 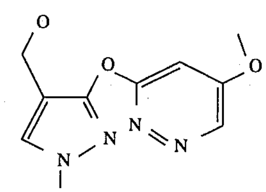 | C 50.84<br>H 5.12<br>N 23.72 | 50.83<br>5.10<br>23.62 |
| 91 | PYRIDAZINE, 3-[[3-(1-FLUOROETHYL)-1-METHYL-1H-PYRAZOL-5-YL]OXY]-5-METHOXY- MP: 87.0–89.0 | 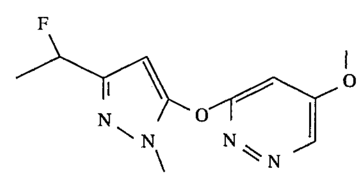 | C 52.38<br>H 5.19<br>N 22.21 | 52.33<br>5.20<br>22.17 |

-continued

| Compound No. | Name | Structure | Analysis (%) Calc'd | Found |
|---|---|---|---|---|
| 92 | PYRIDAZINE, 3-[[3-(DIFLUOROMETHYL)-1-METHYL-1H-PYRAZOL-5-YL]OXY]-5-METHOXY- MP: 127.0–130.0 | 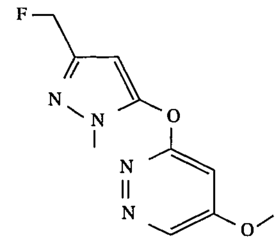 | C 50.42<br>H 4.65<br>N 23.52 | 50.38<br>4.63<br>23.35 |
| 93 | 1H-PYRAZOLE-3-METHANOL, 5-[(5-METHOXY-3-PYRIDAZINYL)OXY]-1-METHYL-ALPHA-(TRIFLUOROMETHYL)- MP: 167.0–168.0 | 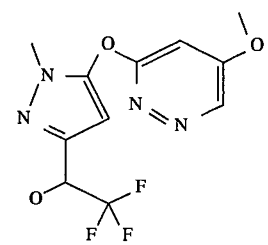 | C 43.43<br>H 3.64<br>N 18.42 | 43.37<br>3.64<br>18.38 |
| 94 | PYRIDAZINE, 5-METHOXY-3-[[1-METHYL-3-(2,2,3,3,4,4,5,5,6,6,7,7,7-TRIDECAFLUORO-1-METHYLENEHEPTYL)-1H-PYRAZOL-5-YL]OXY]- | 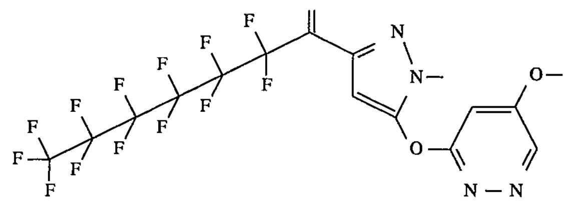 | C 37.11<br>H 2.01<br>N 10.18 | 37.64<br>2.12<br>10.02 |
| 95 | 1H-PYRAZOLE-3-METHANOL, 5-[(5-METHOXY-3-PYRIDAZINYL)OXY]-1-METHYL-ALPHA-(TRIDECAFLUOROHEXYL)-ALPHA-(TRIFLUOROMETHYL)- | 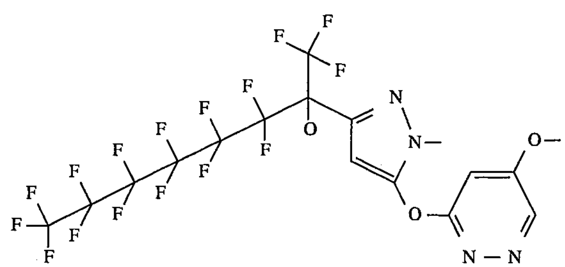 | C 32.81<br>H 1.62<br>N 9.00 | 34.58<br>2.02<br>8.72 |

-continued

| Compound No. | Name | Structure | Analysis (%) Calc'd | Found |
|---|---|---|---|---|
| 96 | PYRIDAZINE, 5-METHOXY-3-[[1-METHYL-3-[1-TRIFLUOROMETHYL)ETHENYL]-1H-PYRAZOL-5-YL]OXY]- MP: 80.0–81.0 | 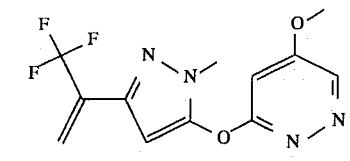 | C 48.01<br>H 3.69<br>N 18.66 | 48.02<br>3.68<br>18.63 |
| 97 | 1H-PYRAZOLE-3-METHANOL, 5-[(5-METHOXY-3-PYRIDAZINYL)OXY]-1-METHYL-ALPHA,ALPHA-BIS(TRIFLUOROMETHYL)- MP: 147.0–148.0 | 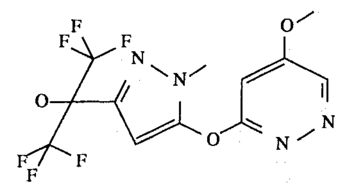 | C 38.72<br>H 2.71<br>N 15.05 | 38.74<br>2.68<br>15.05 |
| 98 | PYRIDAZINE, 3-[[1-(1,1-DIMETHYLETHYL)-3-METHYL-1H-PYRAZOL-5-YL]OXY]-5-METHOXY- MP: 88.0–89.0 | 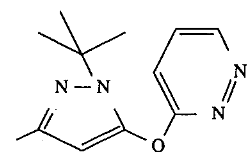 | C 59.53<br>H 6.92<br>N 21.36 | 59.60<br>6.96<br>21.44 |
| 99 | PYRIDAZINE, 3-[[1-(1,1-DIMETHYLETHYL)-3-TRIFLUOROMETHYL)-1H-PYRAZOL-5-YL]OXY]-5-METHOXY- MP: 86.0–87.0 | 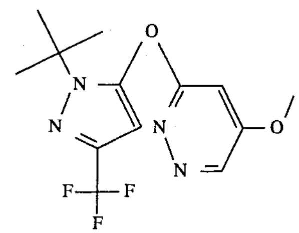 | C 49.37<br>H 4.78<br>N 17.71 | 49.73<br>4.73<br>17.98 |
| 100 | PYRIDAZINE, 3-[[1-(1,1-DIMETHYLETHYL)-3-(PENTAFLUOROETHYL)-1H-PYRAZOL-5-YL]OXY]-5-METHOXY- MP: 107.0–108.0 | 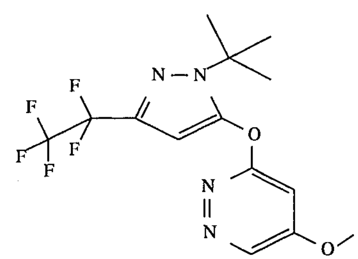 | C 45.91<br>H 4.13<br>N 15.30 | 46.10<br>4.13<br>15.31 |

-continued

| Compound No. | Name | Structure | Analysis (%) | |
|---|---|---|---|---|
| | | | Calc'd | Found |
| 101 | PYRIDAZINE, 5-METHOXY-3-[[1-METHYL-3-(2,2,2-TRIFLUOROETHYL)-1H-PYRAZOL-5-YL]OXY]- MP: 92.0–95.0 | 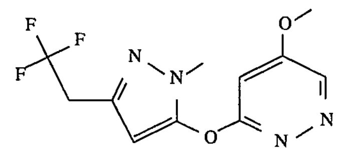 | C 45.84<br>H 3.85<br>N 19.44 | 45.87<br>3.90<br>19.37 |
| 102 | PYRIDAZINE, 3-[[3-(2,2-DIFLUOROETHENYL)-1-METHYL-1H-PYRAZOL-5-YL]OXY]-5-METHOXY- MP: 123.0–125.0 | 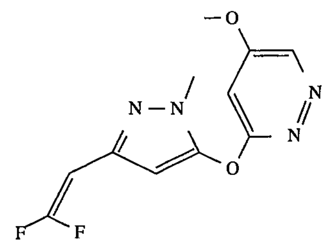 | C 49.26<br>H 3.76<br>N 20.89 | 49.09<br>3.78<br>20.80 |

PRE-EMERGENT ACTIVITY ON PLANTS

As noted above, compounds of this invention have been found to be effective as herbicides, particularly as pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The symbol C represents complete control and N or a hyphen represents no data.

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha) or other rate as indicated in Table A. After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed above the columns according to the following legend:

COBU—Cocklebur
VELE—Velvetleaf
DOBR—Downy Brome
MOGL—Morningglory
BYGR—Barnyardgrass
ANBG—Annual Bluegrass
SEJG—Seedling Johnsongrass*
YENS—Yellow Nutsedge
INMU—Indian Mustard
WIBW—Wild Buckwheat
FOXT—Foxtail
RICE—Rice
CORN—Corn
SOYB—Soybean

* Grown from vegetative propagules

TABLE A

| Ex. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 1 | 11.21 | 0 | 10 | 60 | 20 | 60 | 50 | 10 | 80 | 30 | C |
| 2 | 11.21 | 0 | 0 | 0 | 0 | 0 | 30 | 0 | 30 | 20 | 40 |
|  | 11.21 | 0 | 0 | 0 | 0 | 0 | 50 | 0 | 20 | 10 | 20 |
| 3 | 11.21 | 30 | 70 | 80 | 20 | 80 | 80 | 0 | 30 | 70 | 30 |
| 4 | 11.21 | 0 | 20 | 20 | 0 | 20 | 0 | 0 | 20 | 70 | 20 |
| 5 | 10.09 | 90 | C | C | C | C | C | C | C | C | C |
| 6 | 11.21 | 0 | 60 | 50 | 20 | 50 | 40 | 20 | 20 | 90 | 20 |
| 7 | 11.21 | 90 | C | C | C | C | 90 | C | C | C | C |
| 8 | 11.21 | 40 | 90 | 90 | 30 | C | 90 | 90 | 70 | 90 | 80 |
| 9 | 11.21 | 80 | C | C | C | C | 80 | 50 | 20 | C | C |
| 10 | 11.21 | 80 | 90 | 90 | 80 | C | 90 | 80 | C | C | C |
| 11 | 11.21 | 20 | 90 | 80 | 30 | C | 30 | 20 | 30 | 80 | 30 |
| 12 | 11.21 | 0 | 0 | 0 | 0 | 0 | 0 | 0 | 0 | 30 | 0 |
| 15 | 11.21 | 0 | 0 | 30 | 20 | 70 | 20 | 30 | 40 | 90 | 60 |
| 16 | 11.21 | 80 | C | C | 80 | C | C | 90 | C | C | C |
| 17 | 11.21 | 80 | C | C | C | C | C | C | C | C | C |
| 18 | 1.12 | 90 | C | C | 90 | C | C | C | C | C | C |
| 19 | 1.12 | 70 | C | C | 60 | C | C | 90 | C | C | 80 |
| 20 | 11.21 | 30 | 80 | 70 | 30 | 90 | 80 | 60 | 40 | 90 | 50 |
|  | 1.12 | 0 | 0 | 0 | 0 | 0 | 0 | 0 | 0 | 30 | 0 |
| 21 | 11.21 | 90 | C | C | C | C | C | C | C | C | C |
| 22 | 11.21 | 80 | C | C | 20 | C | C | 70 | 90 | C | C |
| 23 | 11.21 | 60 | 90 | 80 | 30 | C | 80 | 30 | 80 | C | 80 |
| 24 | 11.21 | 70 | 90 | 80 | 30 | C | C | 30 | 90 | C | 90 |
| 25 | 11.21 | 90 | C | C | 30 | C | C | 90 | C | C | C |
| 26 | 11.21 | 0 | 0 | 0 | 0 | 0 | 0 | 0 | 0 | 30 | 0 |
| 27 | 11.21 | 0 | 20 | 20 | 0 | 30 | 30 | 0 | 30 | 50 | 20 |
| 28 | 11.21 | 0 | 0 | 0 | 0 | 0 | 0 | N | 0 | 0 | 0 |
| 29 | 11.21 | 20 | 10 | 0 | 10 | 10 | 20 | 10 | 30 | 30 | 20 |
| 30 | 11.21 | 0 | 0 | 0 | 0 | 20 | 20 | 0 | 0 | 20 | 20 |
| 31 | 11.21 | 10 | 70 | 30 | 20 | 80 | 40 | 20 | 30 | 70 | 0 |
|  | 11.21 | 0 | 50 | 20 | 20 | 20 | 20 | 20 | 20 | 80 | 20 |
| 32 | 11.21 | 0 | 20 | 20 | 20 | 0 | 20 | 30 | 30 | 30 | 0 |
|  | 11.21 | 0 | 20 | 10 | 0 | 20 | 20 | 20 | 0 | 20 | 0 |
| 33 | 11.21 | 80 | C | C | 90 | C | C | C | C | C | C |
| 34 | 11.21 | 90 | C | C | C | C | C | 90 | C | C | C |
| 35 | 11.21 | 40 | C | 80 | 40 | 80 | C | 60 | 90 | C | C |
| 36 | 11.21 | 60 | 20 | 60 | 30 | 30 | 20 | 0 | 50 | C | 50 |
| 37 | 11.21 | 70 | 90 | 80 | 20 | C | 30 | 20 | 40 | C | 60 |
| 38 | 11.21 | C | C | C | C | C | C | 90 | C | C | C |

TABLE A-continued

| Ex. No. | Rate kg/ha | | | | | | | | | | |
|----|-------|-----|---|----|----|----|-----|----|----|----|----|
| 39 | 11.21 | 90 | C | C | C | C | C | 90 | C | C | 90 |
| 40 | 11.21 | 50 | C | C | 90 | C | C | 50 | C | C | 90 |
| 41 | 11.21 | 20 | 30 | 30 | 20 | 20 | 20 | 0 | 30 | C | 0 |
|    | 11.21 | 0 | 0 | 0 | 0 | 0 | 20 | 0 | 20 | C | 0 |
| 42 | 11.21 | 80 | C | 80 | 50 | C | C | 40 | C | C | C |
| 43 | 11.21 | C | C | C | C | C | C | C | C | C | C |
| 45 | 11.21 | 20 | 30 | 20 | 20 | 30 | 80 | 30 | 20 | 80 | 30 |
| 46 | 11.21 | 50 | C | 90 | C | C | C | 90 | 90 | C | 80 |
| 47 | 11.21 | 0 | 0 | 20 | 0 | 90 | 70 | 0 | 70 | 90 | 50 |
| 48 | 11.21 | 0 | 10 | 0 | 0 | 40 | 30 | 0 | 10 | 20 | 20 |
|    | 11.21 | 0 | 0 | 0 | 0 | 20 | 0 | 0 | 0 | 20 | 20 |
| 49 | 11.21 | 0 | 0 | 0 | 0 | 40 | 20 | 10 | 10 | 20 | 10 |
| 50 | 11.21 | 30 | 80 | 80 | 60 | C | 90 | 40 | 80 | C | 70 |
| 51 | 11.21 | 0 | 10 | 0 | 0 | 0 | 0 | 0 | 10 | 70 | 10 |
| 52 | 11.21 | 10 | 0 | 0 | 0 | 10 | 10 | 0 | 10 | 70 | 10 |
| 53 | 11.21 | 20 | 30 | 40 | 0 | C | C | 30 | 80 | 80 | 20 |
| 54 | 11.21 | 80 | C | 90 | 50 | C | C | 80 | 90 | C | 70 |
| 55 | 1.12 | 40 | 70 | 40 | 20 | 60 | C | 60 | 50 | 80 | 90 |
| 56 | 1.12 | 30 | C | 60 | 40 | 60 | 70 | 0 | 60 | 80 | 20 |
|    | 1.12 | 0 | C | 50 | 50 | 0 | 60 | 20 | 60 | 90 | 20 |
| 57 | 11.21 | 0 | 0 | 0 | 0 | 10 | 20 | 10 | 20 | 20 | 30 |
|    | 11.21 | 0 | 0 | 40 | 10 | 70 | 20 | 0 | 0 | 80 | 70 |
| 58 | 11.21 | 50 | 90 | 40 | 0 | 90 | 90 | 50 | 30 | 90 | 30 |
| 59 | 11.21 | 0 | 70 | 20 | 10 | 70 | 80 | 0 | 40 | 90 | 10 |
| 69 | 1.12 | 80 | 80 | 70 | 10 | 0 | 70 | 70 | 30 | 80 | 90 |
| 70 | 11.21 | 0 | 10 | 20 | 0 | 10 | 50 | 0 | 30 | 20 | 10 |
| 71 | 1.12 | 80 | 100 | 20 | 10 | 100 | 100 | 50 | 60 | — | — |

| Ex. No. | Rate kg/ha | FOXT | YENS | BYGR | RICE | CORN | VELE | MOGL | COBU | SOYB |
|----|-------|------|------|------|------|------|------|------|------|------|
| 72 | 1.00 | 0 | 0 | 0 | 0 | 15 | 0 | 0 | 0 | 0 |
| 73 | 1.00 | 0 | 0 | 0 | 0 | 15 | 0 | 0 | 0 | 0 |
| 74 | 1.00 | 45 | 25 | 60 | 0 | 5 | 100 | 80 | 0 | 10 |
|    | 0.20 | 0 | 20 | 0 | 50 | 0 | 80 | 55 | 0 | 10 |
| 75 | 1.12 | | | | | | 0 | | | |
| 76 | 1.00 | 60 | 0 | 20 | 65 | 0 | 30 | 60 | 0 | 0 |
|    | 0.20 | 55 | 50 | 50 | 0 | 30 | 55 | 15 | 50 | 10 |
| 77 | 1.00 | 100 | 85 | 100 | 100 | 65 | 100 | 85 | 80 | 100 |
|    | 0.20 | 70 | 60 | 50 | 0 | 10 | 35 | 50 | 30 | 30 |
| 78 | 1.00 | 65 | 0 | 0 | 0 | 0 | 98 | 85 | 20 | 10 |
|    | 0.20 | 0 | 0 | 0 | 0 | 0 | 0 | 0 | 0 | 0 |
| 79 | 1.00 | 95 | 80 | 95 | 90 | 65 | 100 | 95 | 55 | 95 |
|    | 0.20 | 95 | 70 | 95 | 65 | 20 | 100 | 75 | 50 | 20 |
|    | 0.04 | 90 | 35 | 40 | 40 | 0 | 50 | 0 | 50 | 0 |
|    | 0.008 | 55 | 35 | 20 | 25 | 0 | 15 | 0 | 0 | 0 |
| 80 | 1.00 | 100 | 100 | 100 | 100 | 100 | 100 | 100 | 100 | 100 |
|    | 2.20 | 100 | 90 | 95 | 100 | 75 | 100 | 100 | 25 | 60 |
|    | 0.04 | 95 | 30 | 45 | 20 | 0 | 100 | 45 | 0 | 20 |
|    | 0.008 | 70 | 0 | 25 | 0 | 10 | 50 | 0 | — | 15 |
| 81 | 1.0 | 70 | 10 | 60 | 20 | 0 | 10 | 10 | — | 10 |
|    | 0.20 | 20 | 0 | 0 | 10 | 0 | 0 | 0 | 0 | 0 |
| 82 | 1.0 | 100 | 95 | 100 | 85 | 75 | 100 | 80 | 100 | 60 |
|    | 0.20 | 98 | 55 | 100 | 50 | 0 | 45 | 20 | 35 | 0 |
|    | 0.04 | 98 | 0 | 50 | 30 | 0 | 35 | 0 | 0 | 0 |
| 84 | 5.0 | 99 | 20 | 85 | 20 | 10 | 98 | 90 | 20 | 15 |
|    | 1.0 | 98 | 5 | 50 | 0 | 0 | 30 | 50 | 30 | 20 |
|    | 0.2 | 30 | 0 | 0 | 0 | 0 | 0 | 0 | 0 | 0 |
| 85 | 1.0 | 50 | 65 | 20 | 70 | 0 | 70 | 55 | 25 | 25 |
|    | 0.2 | 80 | 0 | 0 | 0 | 0 | 85 | 20 | 0 | 25 |
| 86 | 5.0 | 95 | 10 | 15 | 0 | 0 | 50 | 40 | 25 | 25 |
|    | 1.0 | 0 | 0 | 0 | 0 | 0 | 20 | 0 | 0 | 15 |
| 87 | 1.0 | 25 | 0 | 0 | 0 | 0 | 0 | 0 | 0 | 0 |
| 88 | 1.0 | 100 | 10 | 10 | 20 | 0 | 100 | 65 | 80 | 25 |
|    | 0.2 | 20 | 0 | 10 | 10 | 0 | 0 | 0 | 0 | 0 |
| 89 | 1.0 | 10 | 0 | 5 | 0 | 0 | 50 | 15 | 0 | 5 |
|    | 0.2 | 0 | 0 | 0 | 0 | 0 | 0 | 5 | 0 | 0 |
| 90 | 1.0 | 0 | 0 | 0 | 0 | 0 | 0 | 0 | 0 | 0 |
| 91 | 1.0 | 15 | 10 | 0 | 0 | 0 | 10 | 0 | 10 | 15 |
|    | 0.2 | 0 | 0 | 0 | 0 | 5 | 5 | 0 | 0 | 0 |
| 92 | 1.12 | 35 | 0 | 0 | — | 0 | 5 | 15 | — | 0 |
| 93 | 1.0 | 100 | 50 | 90 | 0 | 85 | 100 | 100 | 30 | 85 |
|    | 0.2 | 60 | 0 | 0 | 0 | 5 | 50 | 35 | 0 | 5 |
|    | 0.4 | 0 | 0 | 0 | 0 | 0 | 10 | 0 | 0 | 0 |
| 94 | 1.0 | 0 | 0 | 0 | 0 | 0 | 0 | 0 | 0 | 0 |
| 95 | 1.0 | 0 | 0 | 0 | 0 | 0 | 0 | 0 | 0 | 0 |
| 96 | 1.0 | 100 | 50 | 100 | 60 | 50 | 100 | 100 | 60 | 75 |
|    | 0.2 | 100 | 10 | 90 | 30 | 40 | 95 | 50 | 60 | 70 |
|    | 0.04 | 30 | 0 | 0 | 0 | 0 | 30 | 0 | 10 | 0 |

TABLE A-continued

| | | | | | | | | | | |
|---|---|---|---|---|---|---|---|---|---|---|
| 97 | 1.0 | 95 | 30 | 45 | 40 | 20 | 100 | 85 | 30 | 50 |
| | 0.2 | 20 | 0 | 10 | 0 | 0 | 40 | 0 | 0 | 10 |
| 98 | 1.0 | 0 | 20 | 65 | 0 | 0 | 0 | 0 | 0 | 0 |
| | 0.2 | 0 | 20 | 15 | 0 | 0 | 0 | 0 | 0 | 0 |
| 99 | 1.0 | 10 | 0 | 10 | 0 | 0 | 0 | 0 | 0 | 0 |
| 100 | 1.0 | 85 | 10 | 10 | 5 | 15 | 0 | 0 | 0 | 0 |
| | 0.2 | 0 | 0 | 0 | 0 | 0 | 0 | 0 | 0 | 0 |
| 101 | 1.0 | 100 | 60 | 100 | 50 | 40 | 100 | 100 | 90 | 75 |
| | 0.2 | 95 | 0 | 70 | 0 | 0 | 100 | 50 | 90 | 15 |
| | 0.04 | 30 | 0 | 0 | 0 | 0 | 25 | 0 | 0 | 10 |
| 102 | 1.0 | 100 | 70 | 55 | 0 | 5 | 90 | 50 | 10 | 25 |
| | 0.2 | 60 | 15 | 35 | 0 | 0 | 10 | 20 | 0 | 5 |

POST-EMERGENT HERBICIDE ACTIVITY ON PLANTS

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by green-house testing, and the results are shown in the following Table B.

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha or other rate as indicated in Table B while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes and symbols in Table A are the same as above defined.

TABLE B

| CP No. | Rate Kg/ha | Yens | Anbg | Sejg | Dobr | Bygr | Mogl | Cobu | Vele | Inmu | Wibw |
|---|---|---|---|---|---|---|---|---|---|---|---|
| 1 | 11.21 | 0 | 0 | 10 | 0 | 10 | 20 | — | 30 | 20 | 40 |
| 3 | 11.21 | 0 | 0 | 10 | 10 | 10 | 30 | 20 | 30 | 30 | 30 |
| 4 | 11.21 | 0 | 10 | 0 | 0 | 0 | 10 | 0 | 10 | 30 | 20 |
| 5 | 11.21 | 40 | 50 | 40 | 20 | 60 | 50 | 50 | 40 | 60 | 80 |
| 6 | 11.21 | 0 | 10 | 0 | 0 | 0 | 10 | 10 | 20 | 80 | 40 |
| 7 | 11.21 | 50 | 90 | 70 | 30 | 90 | 80 | 80 | 90 | 90 | 90 |
| 8 | 11.21 | 10 | 20 | 30 | 20 | 80 | 50 | 70 | 60 | 80 | 90 |
| 9 | 11.21 | 20 | 50 | 40 | 20 | 60 | 40 | 50 | 50 | 40 | 90 |
| 10 | 11.21 | 30 | 40 | 50 | 20 | 60 | 40 | 50 | 40 | 40 | 80 |
| 11 | 11.21 | 0 | 0 | 0 | 0 | 10 | 10 | 0 | 20 | 20 | 40 |
| 12 | 11.21 | 0 | 0 | 0 | 0 | 0 | 10 | 0 | 0 | 10 | 30 |
| 15 | 11.21 | 0 | 0 | 0 | 10 | 10 | 10 | 50 | 0 | 30 | 20 |
| 16 | 11.21 | 0 | 40 | 40 | 20 | 50 | 30 | 40 | 60 | 50 | 90 |
| 17 | 11.21 | 40 | 90 | 90 | 50 | 70 | 80 | 80 | 60 | 50 | 90 |
| 18 | 1.12 | 60 | C | 60 | 20 | 60 | 60 | 50 | 40 | 40 | 60 |
| 19 | 1.12 | 20 | 90 | 90 | 50 | 80 | 80 | 80 | 80 | 80 | 90 |
| | 1.12 | 40 | 60 | 60 | 40 | 50 | 70 | 60 | 60 | 60 | 80 |
| 20 | 11.21 | 0 | 10 | 0 | 0 | 50 | 30 | 30 | 50 | 40 | 40 |
| 20 | 1.12 | 0 | 0 | 0 | 0 | 20 | 20 | 30 | 30 | 40 | 60 |
| 21 | 11.21 | 20 | 20 | 30 | 0 | 30 | 50 | 50 | 30 | 30 | N |
| 22 | 11.21 | 0 | 0 | 10 | 10 | 10 | 30 | 30 | 70 | 50 | 90 |
| 23 | 11.21 | 0 | 0 | 0 | 0 | 40 | 0 | 0 | C | 40 | 90 |
| 24 | 11.21 | 20 | 30 | 30 | 20 | 30 | 30 | 30 | 40 | 50 | 90 |
| 25 | 11.21 | 0 | 20 | 20 | 20 | 20 | 50 | 30 | 40 | 30 | 50 |
| 26 | 11.21 | 0 | 0 | 0 | 0 | 0 | 0 | 0 | 0 | 0 | 0 |
| 28 | 11.21 | 0 | 0 | 30 | 0 | 0 | 20 | 0 | 30 | 20 | 20 |
| 29 | 11.21 | 0 | 30 | 30 | 0 | 0 | 0 | 0 | 20 | 50 | 20 |
| 30 | 11.21 | 0 | 0 | 20 | 0 | 50 | 20 | 0 | 0 | 0 | 0 |
| 31 | 11.21 | 0 | 0 | 20 | 0 | 0 | 0 | 0 | 0 | 20 | 0 |
| 32 | 11.21 | 0 | 20 | 20 | 0 | 0 | 40 | 0 | 0 | 20 | 20 |
| 33 | 11.21 | 20 | 40 | 40 | 0 | 30 | 40 | 30 | 40 | 30 | 90 |
| 34 | 11.21 | 50 | C | 50 | 40 | 60 | 50 | 50 | 40 | 30 | N |
| 35 | 11.21 | 20 | 10 | 40 | 10 | 50 | 30 | 30 | 30 | 30 | N |
| 36 | 11.21 | 0 | 0 | 0 | 0 | 0 | 0 | 0 | 0 | 0 | 0 |
| 37 | 11.21 | 0 | 0 | 0 | 0 | 0 | 0 | 0 | 0 | 60 | 0 |

TABLE B-continued

| Ex. No. | Rate kg/ha | | | | | | | | | |
|---|---|---|---|---|---|---|---|---|---|---|
| 38 | 11.21 | 60 | 80 | 80 | 30 | 70 | 70 | 60 | 80 | 80 | 60 |
| 39 | 11.21 | 20 | 50 | 60 | 30 | 70 | 80 | 80 | 80 | 80 | 80 |
| 39 | 11.21 | 50 | 90 | 90 | 50 | 90 | 80 | 60 | 80 | 80 | 80 |
| 40 | 11.21 | 20 | 60 | 70 | 20 | 50 | 50 | 20 | 50 | 70 | 60 |
|  | 11.21 | 20 | 50 | 70 | 40 | 40 | 60 | 40 | 40 | 60 | 60 |
| 41 | 11.21 | 0 | 20 | 20 | 20 | 30 | 30 | 20 | 20 | 40 | 50 |
|  | 11.21 | 0 | 0 | 0 | 0 | 30 | 20 | 0 | 0 | 0 | 0 |
| 42 | 11.21 | 0 | 50 | 0 | 0 | 20 | 20 | 40 | 20 | 40 | 80 |
|  | 11.21 | 10 | 30 | 20 | 0 | 20 | 40 | 40 | 20 | 50 | 60 |
| 43 | 11.21 | 50 | 40 | 60 | 40 | 80 | 60 | 60 | 60 | 70 | 70 |
| 45 | 11.21 | 0 | 0 | 0 | 0 | 0 | 20 | 20 | 20 | 20 | 0 |
| 46 | 11.21 | 0 | 30 | 20 | 10 | 20 | 40 | 20 | 30 | 60 | 60 |
| 47 | 11.21 | 0 | 0 | 0 | 0 | 10 | 20 | 10 | 30 | 30 | 30 |
| 48 | 11.21 | 0 | 0 | 0 | 0 | 10 | 30 | 10 | 20 | 20 | 20 |
| 49 | 11.21 | 0 | 0 | 0 | 0 | 10 | 30 | 30 | 40 | 40 | 20 |
| 50 | 11.21 | 0 | 20 | 30 | 10 | 30 | 50 | 40 | 40 | 60 | 70 |
| 51 | 11.21 | 0 | 0 | 0 | 0 | 0 | 30 | 20 | 20 | 30 | 0 |
| 52 | 11.21 | 0 | 0 | 0 | 0 | 0 | 10 | 0 | 0 | 10 | 0 |
| 53 | 11.21 | 0 | 0 | 0 | 0 | 0 | 20 | 10 | 0 | 10 | 0 |
| 54 | 11.21 | 0 | 10 | 20 | 0 | 30 | 60 | 30 | 60 | 50 | 50 |
| 55 | 1.12 | 10 | 40 | 20 | 0 | 10 | 50 | 40 | 20 | 30 | 20 |
| 56 | 1.12 | 0 | 90 | 30 | 10 | 20 | 60 | 50 | 20 | 40 | N |
| 57 | 11.21 | 0 | 10 | 0 | 0 | 50 | 70 | 50 | 70 | 50 | 40 |
| 58 | 11.21 | 0 | 0 | 10 | 0 | 0 | 30 | 30 | 40 | 20 | 20 |
| 59 | 11.21 | 0 | 0 | 0 | 0 | 20 | 40 | 20 | 20 | 40 | 10 |
| 69 | 1.12 | 0 | 10 | 30 | 10 | 10 | 40 | 50 | 50 | 20 | 0 |
| 70 | 11.21 | 0 | 70 | 50 | 50 | 60 | 80 | 50 | — | — | — |
| 72 | 5.6 | 60 | 70 | — | — | — | — | — | — | — | — |

| Ex. No. | Rate kg/ha | FOXT | YENS | BYGR | RICE | CORN | VELE | MOGL | COBU | SOYB |
|---|---|---|---|---|---|---|---|---|---|---|
| 73 | 1.0 | 0 | 0 | 0 | 0 | 0 | 0 | 0 | 0 | 0 |
| 76 | 1.0 | 0 | 0 | 15 | 0 | 0 | 10 | 15 | 0 | 5 |
| 77 | 1.0 | 60 | 25 | 35 | 0 | 0 | 80 | 90 | 75 | 40 |
|  | 0.2 | 0 | 0 | 0 | 0 | 0 | 50 | 0 | 5 | 10 |
| 78 | 1.0 | 30 | 0 | 0 | 0 | 5 | 15 | 50 | 50 | 50 |
|  | 0.2 | 5 | 0 | 0 | 0 | 5 | 0 | 50 | 35 | 25 |
| 79 | 1.0 | 85 | 60 | 45 | 0 | 15 | 85 | 90 | 85 | 75 |
|  | 0.2 | 10 | 0 | 5 | 0 | 15 | 65 | 75 | 70 | 85 |
|  | 0.04 | 0 | 0 | 0 | 0 | 0 | 40 | 65 | 45 | 65 |
| 80 | 1.0 | 100 | 50 | 65 | 0 | 50 | 80 | 85 | 80 | 90 |
|  | 0.2 | 30 | 0 | 0 | 20 | 10 | 60 | 85 | 80 | 85 |
|  | 0.04 | 0 | 15 | 0 | 0 | 0 | 50 | 75 | 75 | — |
| 81 | 1.0 | 0 | 0 | 0 | 0 | 5 | 15 | 40 | 50 | 30 |
|  | 0.2 | 10 | 35 | 0 | 0 | 15 | 70 | 60 | 25 | 40 |
| 82 | 1.0 | 80 | 35 | 80 | 65 | 20 | 80 | 80 | 80 | 100 |
|  | 0.2 | 35 | 0 | 35 | 50 | 0 | 65 | 70 | 80 | 75 |
|  | 0.04 | 25 | 0 | 25 | 0 | 0 | 40 | 60 | 55 | 50 |
| 84 | 5.0 | 15 | 0 | 0 | 0 | 10 | 45 | 75 | 70 | 60 |
| 85 | 1.0 | 0 | 20 | 0 | 0 | 10 | 65 | 75 | 70 | 75 |
|  | 0.2 | 0 | 15 | 0 | 0 | 15 | 30 | 50 | 20 | 35 |
| 86 | 5.0 | 60 | 70 | 20 | 0 | 5 | 10 | 25 | 50 | 20 |
|  | 1.0 | 25 | 0 | 5 | 0 | 0 | 0 | 45 | 35 | — |
| 87 | 1.0 | 0 | 0 | 0 | 0 | 5 | 0 | 35 | 15 | 45 |
|  | 0.2 | 0 | 0 | 0 | 0 | 0 | 0 | 10 | 10 | 5 |
| 88 | 1.0 | 15 | 0 | 0 | 10 | 15 | 25 | 20 | — | — |
| 89 | 1.0 | 0 | 0 | 0 | 0 | 5 | 36 | 30 | 20 | 40 |
| 90 | 1.0 | 0 | 0 | 0 | 0 | 0 | 0 | 5 | 0 | 5 |
| 91 | 1.0 | 10 | 0 | 0 | 0 | 0 | 35 | 25 | 25 | 35 |
|  | 0.2 | 0 | 35 | 0 | 0 | 0 | 10 | 10 | 0 | 15 |
| 93 | 1.0 | 20 | 10 | 0 | 20 | 10 | 60 | 75 | 50 | 60 |
| 94 | 1.0 | 70 | 35 | 25 | 65 | 10 | 35 | 65 | 80 | 35 |
| 95 | 1.0 | 0 | 0 | 0 | 0 | 5 | 0 | 5 | 45 | 0 |
| 96 | 1.0 | 80 | 25 | 10 | 10 | 5 | 65 | 50 | 80 | 90 |
|  | 0.2 | 40 | 0 | 10 | 0 | 5 | 75 | 50 | 50 | 55 |
|  | 0.04 | 0 | 0 | 0 | 0 | 0 | 25 | 25 | 60 | 25 |
| 97 | 1.0 | 0 | 0 | 0 | 30 | — | — | — | — | — |
| 98 | 1.0 | 0 | 0 | 0 | 0 | 0 | 0 | 0 | 0 | 5 |
| 99 | 1.0 | 0 | 0 | 0 | 0 | 0 | 35 | 25 | 0 | 10 |
| 100 | 1.0 | 0 | 0 | 0 | 0 | 5 | 10 | 50 | 0 | 10 |
| 101 | 1.0 | 90 | 10 | 5 | 0 | 5 | — | — | — | — |
| 102 | 1.0 | 0 | 0 | 0 | 20 | 10 | 35 | 30 | 40 | 80 |

As can be seen from the data above, some of the compounds are suitably safe on certain crops and can thus be used for selective control of weeds in these crops. Known safeners can be added to the formulated herbicidal formulation when additional crop safening is indicated.

The methods of making such compositions are well known. Solutions are prepared by simply mixing the ingredients to be included therein. Fine solid compositions are made by blending and, usually, grinding as in a hammer or fluid energy mill. Suspensions are prepared by wet milling, for example. Granules and pellets can be made by spraying the material containing the active material upon preformed granular carriers or by agglomeration techniques or the like.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsions of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents, together with a surface active agent. Suitable solvents for the active ingredient of this invention include N,-N-dimethylformamide, dimethylsulfoxide, N-methyl-pyrrolidone, hydrocarbons and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives
2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido (1,2-d:α',1'-c)-pyrazidiinium salt
5-Bromo-3-isopropyl-6-methyluracil 1,1'-dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea 3-(3,4-Dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)aminocarbonyl]-benezensulfonamide
Methyl-2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2-((4,6-dimethoxy pyrimidin-2-yl)aminocarbonyl)amino) sulfonyl methyl) benzoate
Methyl 2-(((((4-methoxy-6-methyl-l,3,5-triazin-2yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-Propyl N,N-dipropylthiolcarbamate
S-2,3,3-Trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]phenyl]acetamide N-isopropyl-2-chloroacetanilide
2',6'-Diethyl-N-methoxymethyl-2-chloroacetanilide (aka alachlor)
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide
2-Chloro-N-ethoxymethyl-6'-ethylacet-o-toluidide (aka acetochlor)
2-Chloro-6'-ethyl-N-(2-methoxy-1-methylethyl)acet-o-toluidide (aka as metolachlor)
2-Chloro-N-isopropylacetanilide (aka as propachlor)
S-4-Chloro-N-isopropylcarbaniloylmethyl-O,O-dimethyl phosphorothioate (aka anilofos)
N-Butoxymethyl-2-chloro-2',6'-diethylacetanilide (aka butachlor)
3-(4-Bromo-3-chlorophenyl)-1-methoxy-1-methylurea (aka chlorbromuron)
N-Chloroacetyl-N-(2,6-diethylphenyl)glycine (aka diethatyl)
2-Chloro-N-(2-methoxyethyl)acet-2',6'-xylidide (aka dimethachlor)

Preferred are herbicide mixtures of the 3-pyrazolyloxypyridazine and one or more of a just-mentioned 2-chloroacetanilides. Especially, preferred 2-chloroacetanilides include acetochlor, alachlor, butachlor and metolachlor. The preferred ratio of pyridazine to 2-chloroacetanilide is between 10:1 and 1:10.

Acids/Esters/Alcohols 2,2-Dichloropropionic acid
2-Methyl-4-chlorophenoxyacetic acid
2,Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts
Butyl 2-[4-[[5-(trifluoromethyl)-2-pyridinyl]oxy]phenoxy] propanoate Ethers 2,4-Dichlorophenyl-4-nitrophenyl ether
2-Chloro-α,α,α-trifluoro-p-tolyl-3-ethoxy-4-nitrodiphenyl ether
5-(2-Chloro-4-trifluoromethylphenoxy)-N-methyl sulfonyl-2-nitrobenzamide
1'-(Carboethoxy) ethyl 5-[2-chloro-4-(trifluoromethyl)phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-Oxabicyclo (2.2.1) heptane, 1-methyl-4-(1-methylethyl)-2-(2-methylphenylmethoxy)-, exo Fertilizers useful in combination with the active ingredients include, for example, ammonium nitrate, urea, potash and superphosphate. Other useful additaments include materials in which plant organisms take root and grow such as compost, manure, humus, sand and the like.

It is common practice to use various antidotal or safening compounds to reduce the phytotoxicity of certain herbicides to various crops, especially corn. Accordingly, together with the 3-pyrazolyl-oxypyridazines of the present invention, alone or in combination with a herbicidal 2-chloroacetanilide, one can include in the formulations a safening amount of a suitable antidotal compound. Among suitable safeners for inclusion in the formulations of the present invention are fluorazole, cyometrinal, oxabetrinil, dichlormid, AD-67, 1,3-oxazolidine dichloroacetamides and other compounds known in the art as antidotes for herbicides, especially for corn. One preferred safener is 3-(dichloroacetyl)-5-(2-furanyl)-2,2-dimethyl oxazolidine.

Herbicidal formulations of the types described above are exemplified in several illustrative embodiments below.

| | Weight Percent |
|---|---|
| I. Emulsifiable Concentrates | |
| A. Compound of Example No. 13 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
| | 100.00 |
| B. Compound of Example No. 23 | 25.00 |
| Free acid of complex organic phosphate or aromatic or aliphatic hydrophobe base (e.g., GAFAC RE-610) | 5.00 |
| Polyoxyethylene/polyoxyproplene | 1.60 |

|  | Weight Percent |
| --- | --- |
| block copolymer with butanol (e.g., Tergitol XH) | |
| Phenol | 4.75 |
| Monochlorobenzene | 63.65 |
|  | 100.00 |
| II. Flowables | |
| A. Compound of Example No. 12 | 25.00 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
|  | 100.00 |
| B. Compound of Example No. 4 | 45.0 |
| Methyl cellulose | 0.3 |
| silica aerogel | 1.5 |
| Sodium lignosulfonate | 3.5 |
| Sodium N-methyl-N-oleyl taurate | 2.0 |
| Water | 47.7 |
|  | 100.00 |
| III. Wettable Powders | |
| A. Compound of Example No. 16 | 25.0 |
| Sodium lignosulfonate | 3.0 |
| Sodium N-methyl-N-oleyl-taurate | 1.0 |
| Amorphous silica (synthetic) | 71.0 |
|  | 100.00 |
| B. Compound of Example 20 | 80.00 |
| Sodium dioctyl sulfosuccinate | 1.25 |
| Calcium lignosulfonate | 2.75 |
| Amorphous silica (synthetic) | 16.00 |
|  | 100.00 |
| C. Compound of Example No. 6 | 10.0 |
| Sodium lignosulfonate | 3.0 |
| Sodium N-methyl-N-oleyl-taurate | 1.0 |
| Kaolinte clay | 86.0 |
|  | 100.00 |
| IV. Dusts | |
| A. Compound of Example No. 11 | 2.0 |
| Attapulgite | 98.0 |
|  | 100.00 |
| B. Compound of Example No. 8 | 60.0 |
| Montmorillonite | 40.0 |
|  | 100.00 |
| C. Compound of Example No. 19 | 30.0 |
| Ethylene glycol | 1.0 |
| Bentonite | 69.0 |
|  | 100.00 |
| D. Compound of Example No. 13 | 1.0 |
| Diatomaceous earth | 99.0 |
|  | 100.00 |
| V. Granules | |
| A. Compound of Example No. 6 | 15.0 |
| Granular attapulgite (20/40 mesh) | 85.0 |
|  | 100.00 |
| B. Compound of Example No. 7 | 30.0 |
| Diatomaceous earth (20/40) | 70.0 |
|  | 100.00 |
| C. Compound of Example No. 8 | 1.0 |
| Ethylene glycol | 5.0 |
| Methylene blue | 0.1 |
| Pyrophyllite | 93.9 |
|  | 100.00 |
| D. Compound of Example No. 9 | 5.0 |
| Pyrophyllite (20/40) | 95.0 |
|  | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One Y is $C_1$–$C_7$ alkoxy; or an agriculturally acceptable salt thereof.

2. A compound according to claim 1 wherein Y is in the 5-position and n is 1.

3. A compound according to claim 2 wherein Y is methoxy.

4. A compound according to claim 1 wherein the haloalkyl which is X is trifluoromethyl, pentafluoroethyl or heptafluoropropyl.

5. A compound according to claim 1 wherein Z is $C_1$–$C_{10}$ alkyl.

6. A compound according to claim 5 wherein Z is methyl or ethyl.

7. A herbicidal composition comprising a carrier and a herbicidally-effective amount of a compound having the structural formula:

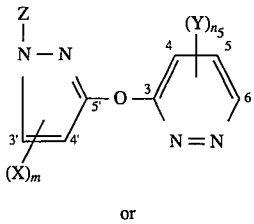

or

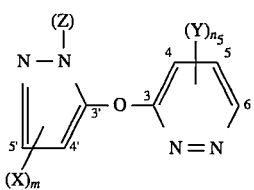

Wherein m and n are each 1;
Z is hydrogen or $C_1$–$C_{10}$ alkyl or $C_1$–$C_3$ haloalkyl;
X is $C_1$–$C_3$ haloalkyl;
either N in the pyridazine ring is optionally substituted with N-oxide;
Y is $C_1$–$C_7$ alkoxy; or an agriculturally acceptable salt thereof.

8. The composition of claim 7 wherein Y in the active compound is in the 5-position and n is 1.

9. The composition of claim 8 wherein Y in the active compound is methoxy.

10. The composition of claim 7 wherein the haloalkyl in the active compound is trifluoromethyl, pentafluoroethyl, or heptafluoropropyl.

11. The composition of claim 7 wherein Z is $C_1$–$C_{10}$ alkyl.

12. The composition of claim 11 wherein Z is methyl or ethyl.

13. A herbicidal method comprising applying to a plant locus a herbicidally-effective amount of a compound having one of the structural formula

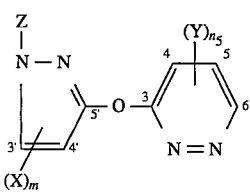

or

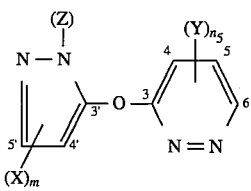

Wherein m and n are each 1;
Z is hydrogen, $C_1$–$C_{10}$ alkyl or $C_1$–$C_3$ haloalkyl;
X is $C_1$–$C_3$ haloalkyl;
either N in the pyridazine ring is optionally substituted with N-oxide;
Y is $C_1$∝$C_7$ alkoxy; or an agriculturally acceptable salt thereof.

14. The method according to claim 13 wherein Y is in the 5-position and n is 1.

15. The method according to claim 14 wherein Y is methoxy.

16. The method according to claim 13 wherein the haloalkyl is trifluoromethyl, pentafluoroethyl or heptafluoropropyl.

17. The method according to claim 13 wherein Z is $C_1$–$C_{10}$ alkyl.

18. The method according to claim 17 wherein Z is methyl or ethyl.

19. 5-Methoxy-3-[[1-methyl-3-(trifluoromethyl)-1H-pyrazol-5-yl]-oxy]-pyridazine.

20. 5-Methoxy-3-[[1-methyl-5-(trifluoromethyl)-1H-pyrazol-3-yl]oxy]-pyridazine.

21. 5-Methyl-3-[[1-methyl-3-(trifluoromethyl)-1H-pyrazol-5-yl]-oxy]-pyridazine.

22. 4-Methyl-3-[[1-methyl-3-(trifluoromethyl)-1H-pyrazol-5-yl]-oxy]-pyridazine.

23. 5-(Methylthio)-3-[[1-methyl-3-(trifluoromethyl)-1H-pyrazol-5-yl]-oxy]-pyridazine.

24. N-methyl-6-[[1-methyl-3-(trifluoromethyl)-1H-pyrazol-5-yl]-oxy]-pyridazine.

25. 3-[[3-(Heptafluoropropyl)-1-methyl-1H-pyrazol-5-yl]-5-methoxypyridazine.

26. 3-[[1-Ethyl-3-(trifluoromethyl)-1H-pyrazol-5-yl]-oxy]-5-methoxypyridazine.

* * * * *